(12) United States Patent
Kotwal

(10) Patent No.: US 7,749,963 B2
(45) Date of Patent: Jul. 6, 2010

(54) ISOLATED RECOMBINANT VACCINIA VIRUS COMPLEMENT CONTROL PROTEIN (HRVCP) POLYPEPTIDE

(76) Inventor: Girish J. Kotwal, 4664 Shenandoah Dr., Louisville, KY (US) 40241

( * ) Notice: Subject to any disclaimer, the term of this patent is extended or adjusted under 35 U.S.C. 154(b) by 0 days.

(21) Appl. No.: 11/917,298

(22) PCT Filed: Jun. 15, 2006

(86) PCT No.: PCT/IB2006/051918

§ 371 (c)(1),
(2), (4) Date: Sep. 8, 2008

(87) PCT Pub. No.: WO2006/136982

PCT Pub. Date: Dec. 28, 2006

(65) Prior Publication Data

US 2008/0318858 A1 Dec. 25, 2008

Related U.S. Application Data

(60) Provisional application No. 60/691,864, filed on Jun. 17, 2005.

(51) Int. Cl.
*A61K 38/16* (2006.01)
*C07K 14/07* (2006.01)
*C12N 15/39* (2006.01)

(52) U.S. Cl. .................. 514/12; 435/235.1; 435/440; 435/69.1; 424/186.1; 424/232.1; 424/278.1; 530/350; 536/23.72

(58) Field of Classification Search .................. None
See application file for complete search history.

(56) References Cited

U.S. PATENT DOCUMENTS 5,157,110 A 10/1992 Kotwal et al.
5,187,268 A 2/1993 Kotwal et al.

OTHER PUBLICATIONS

Rosengard et al., "Variola virus immune evasion design: Expression of a highly efficient inhibitor of human complement," Proceedings of the National Academy of Sciences of USA, National Academy of Science, vol. 99, No. 13, 2002, pp. 8808-8813. (Cited in IDS).*
Sfyroera et al., "Electrostatic Modeling Predicts the Activities of Orthopoxvirus Complement Control Proteins," Journal of Immunology, vol. 174, No. 4, 2005, pp. 2143-2151. (Cited in IDS).*
Cuilla et al ("Evolutionary history of orthopoxvirus proteins similar to human complement regulators", Gene 355:40-47, Aug. 2005).*
Sfyroera et al (Journal of Immunology 174:2143-2151, Feb. 2005, in IDS).*
Rosengard et al (PNAS 99:8808-8813, 2002, in IDS).*
Ganesh et al (PNAS 101:8924-2929, 2004, in IDS).*
Mollnes et al (Molecular Immunology 43:107-121, 2006).*
Batzer et al., "Enhanced evolutionary PCR using oligonuclotides with inosine at the 3'-terminus," Nucleic Acid Res, vol. 19, 1991, p. 5081.

Ganesh et al., "Structure of vaccinia complement protein in complex with heparin and potential implications for complement regulation," Proceedings of the National Academy of Sciences of the United States of America, vol. 101, No. 24, 2004, pp. 8924-8929.
Ghebremariam et al., "Humanized Recombinant Vaccinia Virus Complement Control Protein (hrVCP) with Three Amino Acid Changes, H98Y, E102K, and E120K Creating an Additional Putative Heparin Binding Site, Is 100-fold More Active Than rVCP in Blocking Both Classical and Alternative Complement Pathways," Annals of the New York Academy of Sciences United States, vol. 1056, 2005, pp. 113-122.
Jha et al, "Vaccinia complement control protein: Multi-functional protein and a potential wonder drug," Journal of Biosciences, Indian Academy of Sciences, vol. 28, No. 3, 2003, pp. 265-271.
Jha et al., "Vaccinia virus complement control protein ameliorates collagen-induced arthritis in mice," Molecular Immunology, abstract, vol. 40, No. 2-4, 2003, p. 181.
Kotwal et al., "Vaccinia virus encodes a secretory polypeptide structurally related to complement control proteins," Nature, vol. 335 (6186), 1988, pp. 176-178.
Kotwal et al., "Vaccinia virus Encodes Two Proteins That Are Structurally Related to Members of the Plasma Serine Protease Inhibitor Superfamily," J. Virol., vol. 63, 1989, pp. 690-696.
Kotwal et al., "Inhibition of the Complement Cascade by the Major Secretory Protein of Vaccinia Virus," Science, vol. 250(4982), 1990, pp. 827-830.
McKenzie et al., "Regulation of Complement Activity by Vaccinia Virus Complement-Control Protein," J. Infect. Dis., vol. 166, 1992, pp. 1245-1250.
Murthy et al., "Crystal Structure of a Complement Control Protein that Regulates Both Pathways of Complement Activation and Binds Heparan Sulfate Proteoglycans," Cell, vol. 104, 2001, pp. 301-311.
Ohtsuka et al., "An Alternative Approach to Deoxyoligonucleotides as Hybridization Probes by Insertion of Deoxyinosine at Ambiguous Codon Positions," J Biol Chem, vol. 260, 1985, pp. 2605 2608.
Rosengard et al., "Variola virus immune evasion design: Expression of a highly efficient inhibitor of human complement," Proceedings of the National Academy of Sciences of USA, National Academy of Science, vol. 99, No. 13, 2002, pp. 8808-8813.
Rossolini et al., "Use of deoxyinosine-containing primers vs degenerate primers for polymerase chain reaction based on ambiguous sequence information," Mol Cell Probes, vol. 8, 1994, pp. 91-98.
Sahu et al., "Interaction of Vaccinia Virus Complement Control Protein with Human Complement Proteins: Factor I-Mediated Degradation of C3b to iC3b1 Inactivates the Alternative Complement Pathway," J. Immunol., vol. 160, 1998, pp. 5596-5604.

(Continued)

*Primary Examiner*—Mary E Mosher
(74) *Attorney, Agent, or Firm*—Stites & Harbison PLLC; Terry L. Wright

(57) ABSTRACT

An isolated recombinant vaccinia virus complement control protein (hrVCP) polypeptide comprises a modified amino acid sequence comprising one or more amino acid substitutions to an amino acid sequence as set forth in SEQ ID NO: 2. The hrVCP polypeptide exhibits a complement activation regulatory activity greater than a complement activation regulatory activity of a polypeptide comprising the amino acid sequence as set forth in SEQ ID NO: 2. The one or more amino acid substitutions are selected from the group consisting of H98Y, E102K, E108K, E120K, and combinations thereof.

27 Claims, 17 Drawing Sheets

OTHER PUBLICATIONS

Figure 1:
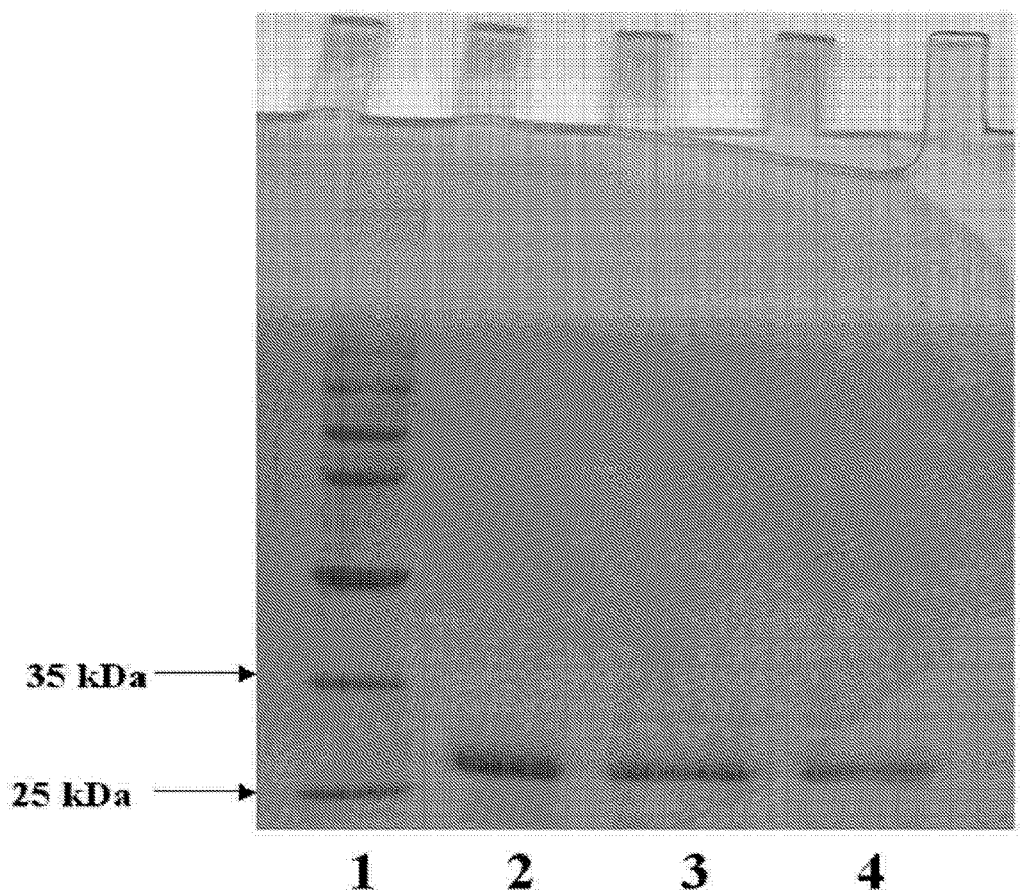

Sfyroera et al., "Electrostatic Modeling Predicts the Activities of Orthopoxvirus Complement Control Proteins," Journal of Immunology, vol. 174, No. 4, 2005, pp. 2143-2151.

Smith et al., "Conserved Surface-Exposed K/R-X-K/R Motifs and Net Positive Charge on Poxvirus Complement Control Proteins Serve as Putative Heparin Binding Sites and Contribute to Inhibition of Molecular Interactions with Human Endothelial Cells: a Novel Mechanism for Evasion of Host Defense," J. Virol., vol. 74, No. 12, 2000, pp. 5659-5666.

Smith et al., "Mapping of regions within the vaccinia virus complement control protein involved in dose-dependent binding to key complement components and heparin using surface plasmon resonance," Biochim, Biophys. Acta, vol. 1650, 2003, pp. 30-39.

Walport, M.J., "Complement," N. Eng. J. Med., vol. 344, No. 14, 2001, pp. 1058-1066 and N. Eng. J. Med., vol. 344, No. 15, 2001, pp. 1140-1144.

ISA/European Patent Office, International Search Report and Written Opinion for international application No. PCT/IB2006/051918, completed Apr. 17, 2007.

* cited by examiner

FIG 2A

Inhibition of CP by rVCP/hrVCPs

FIG 2B

Comparison of rVCP/hrVCPs Potency in inhibiting CP

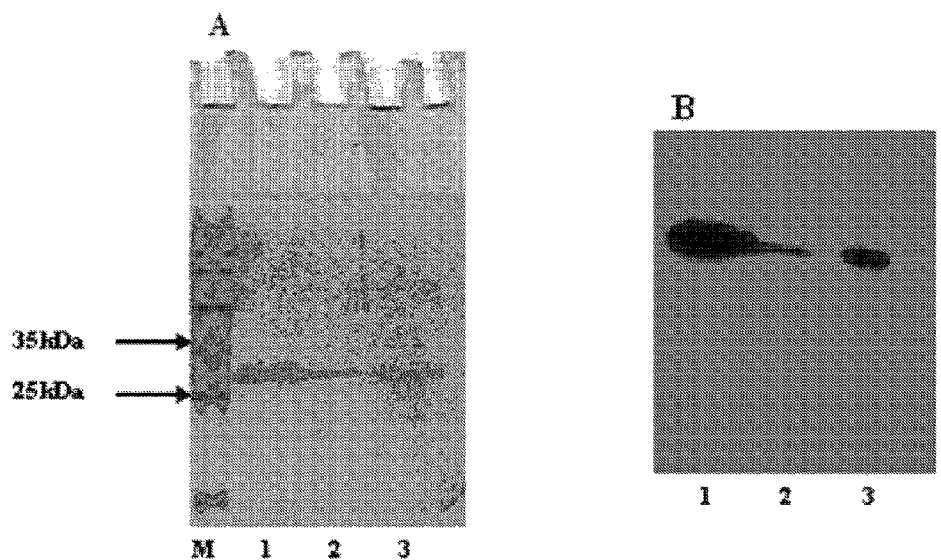
FIG 5A&B
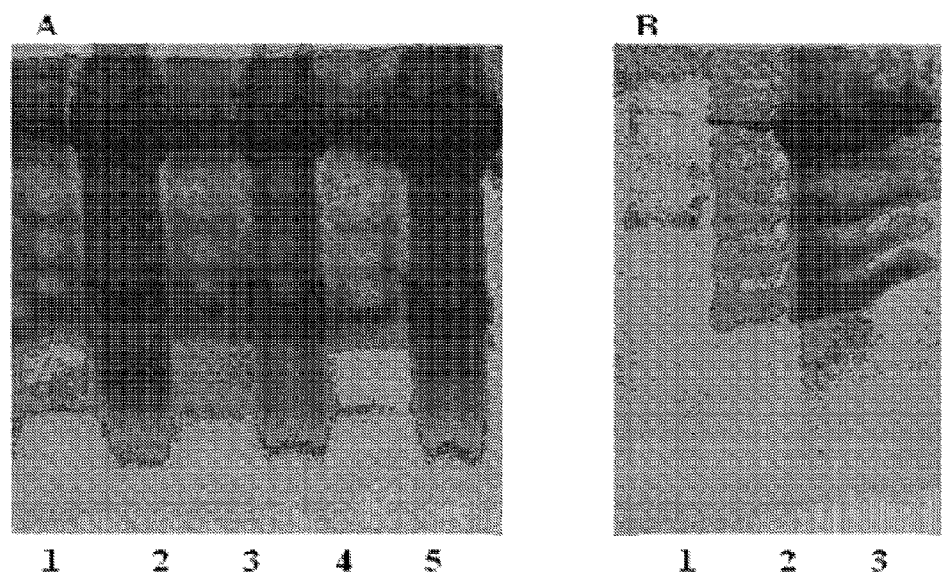
FIG 6A&B

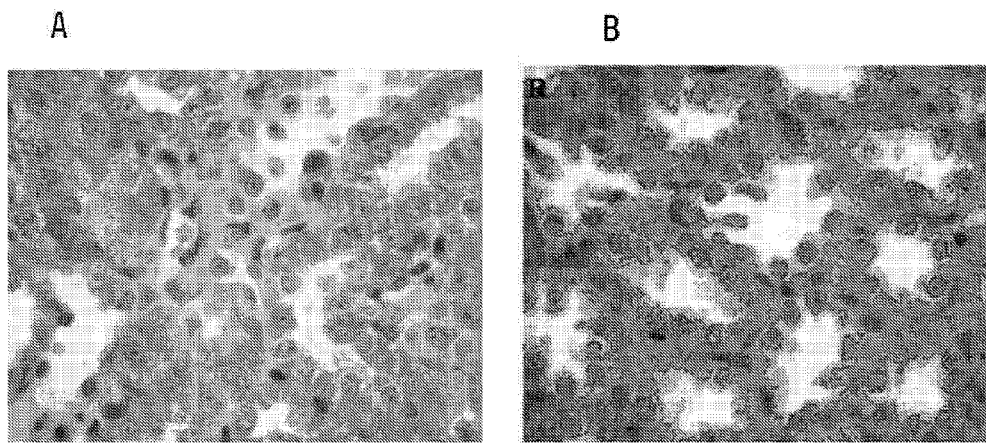
FIG 8A&B
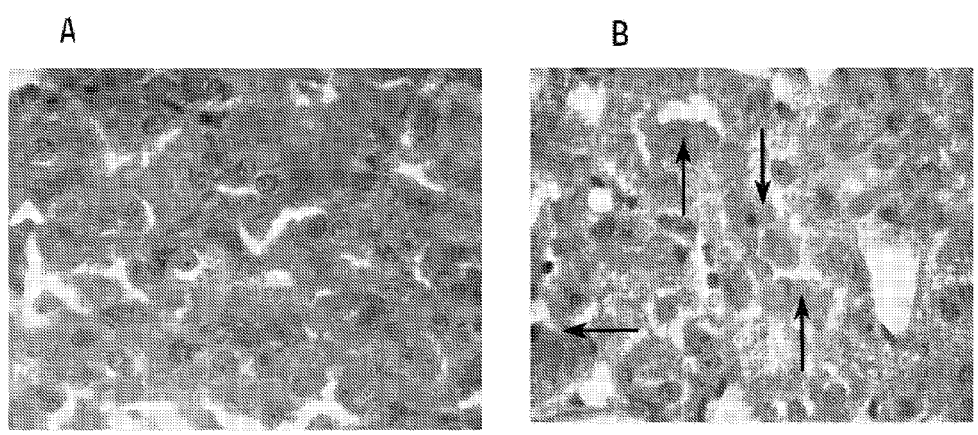
FIG 9A&B

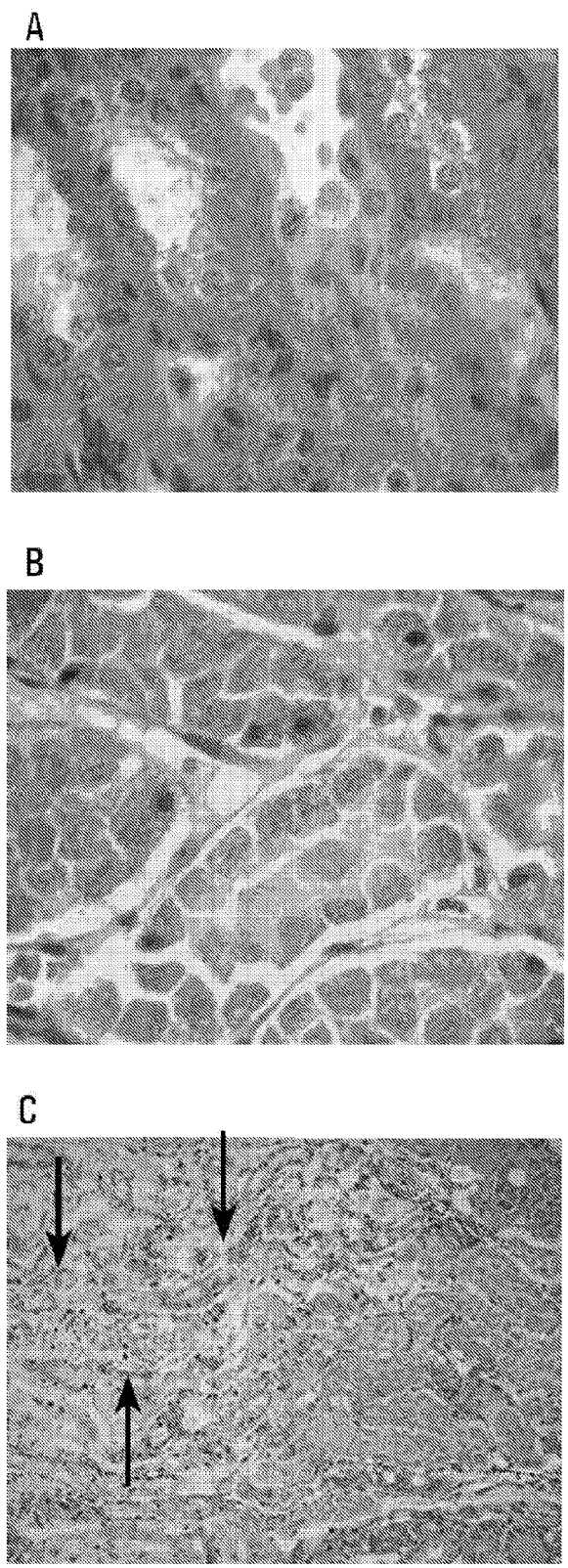
FIG 10A, B&C

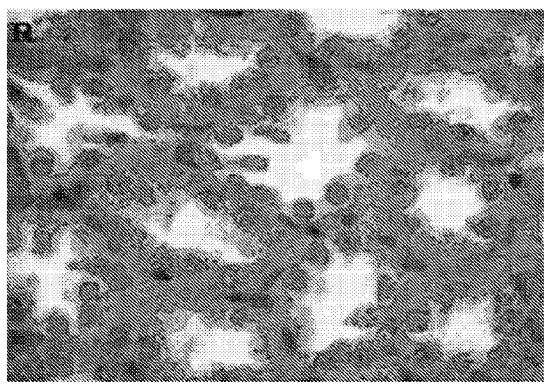
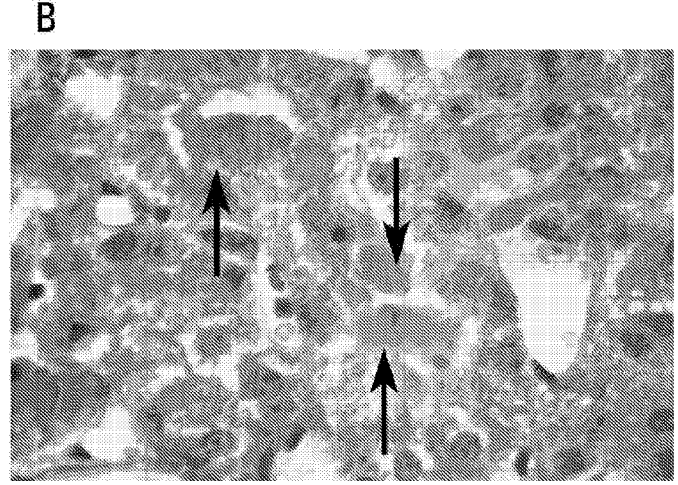
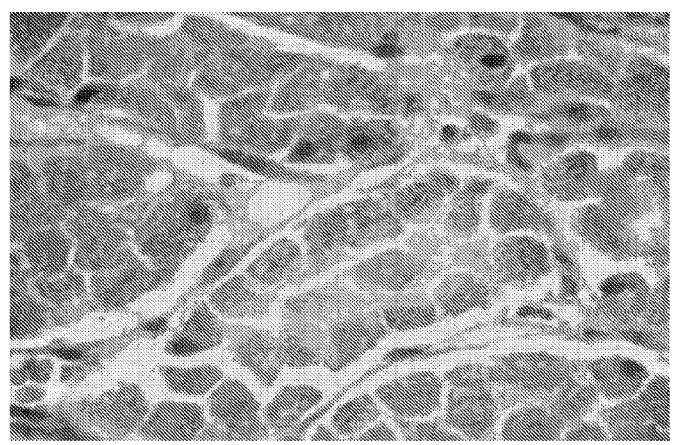
FIG 11A,B&C

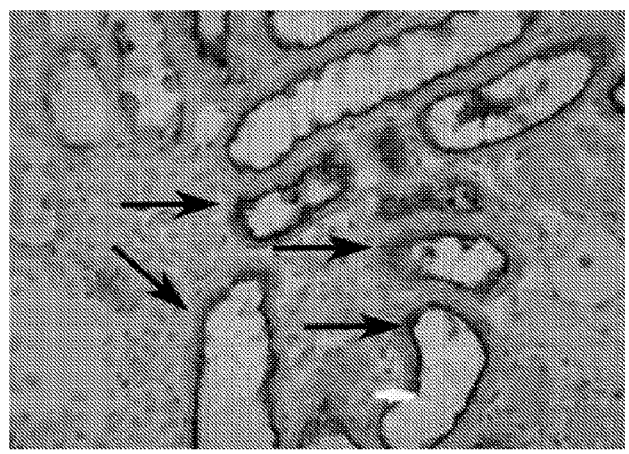
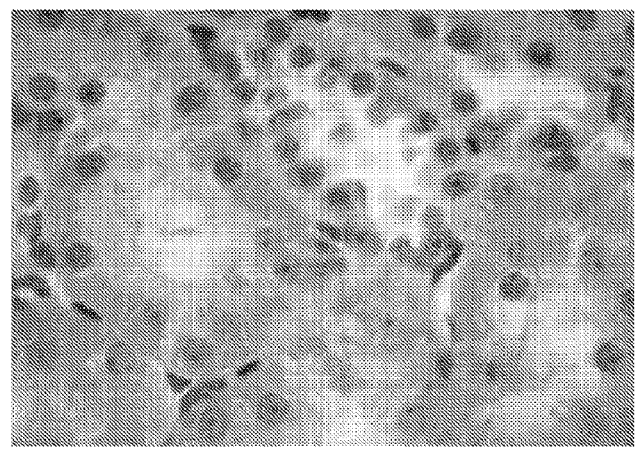
FIG 12A&B

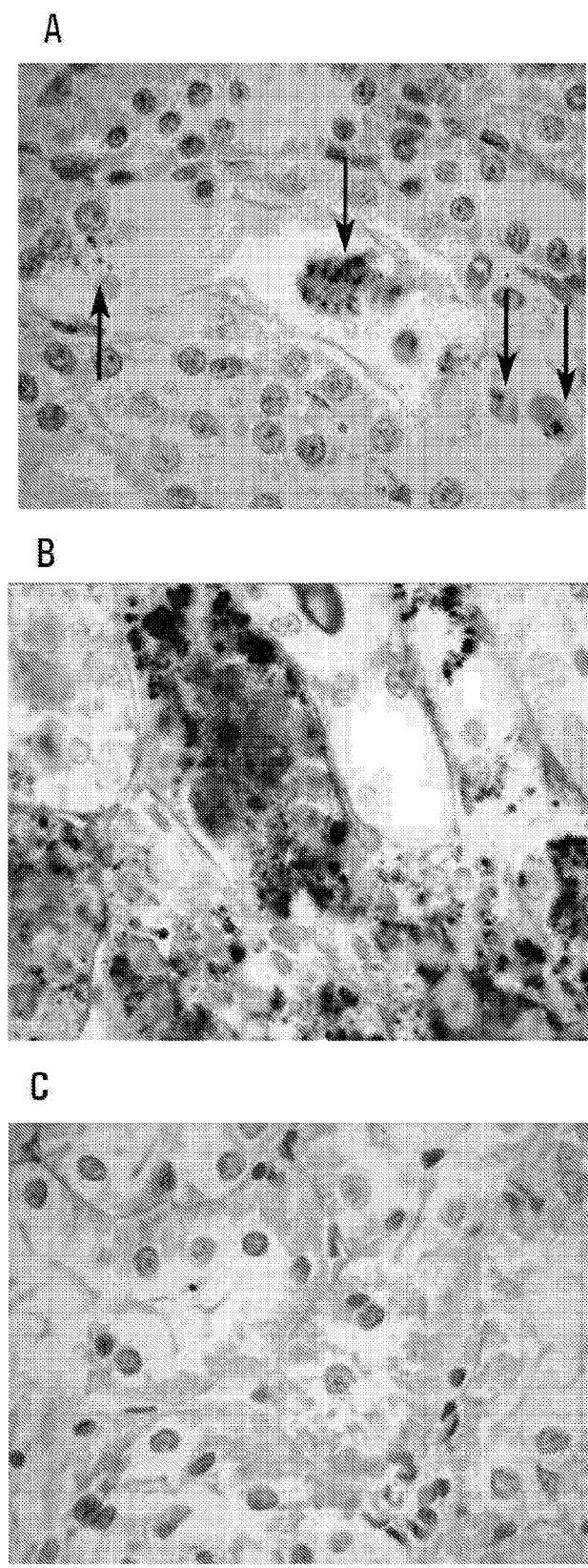
FIG 13a,b&C

FIG 16A,B,C&D

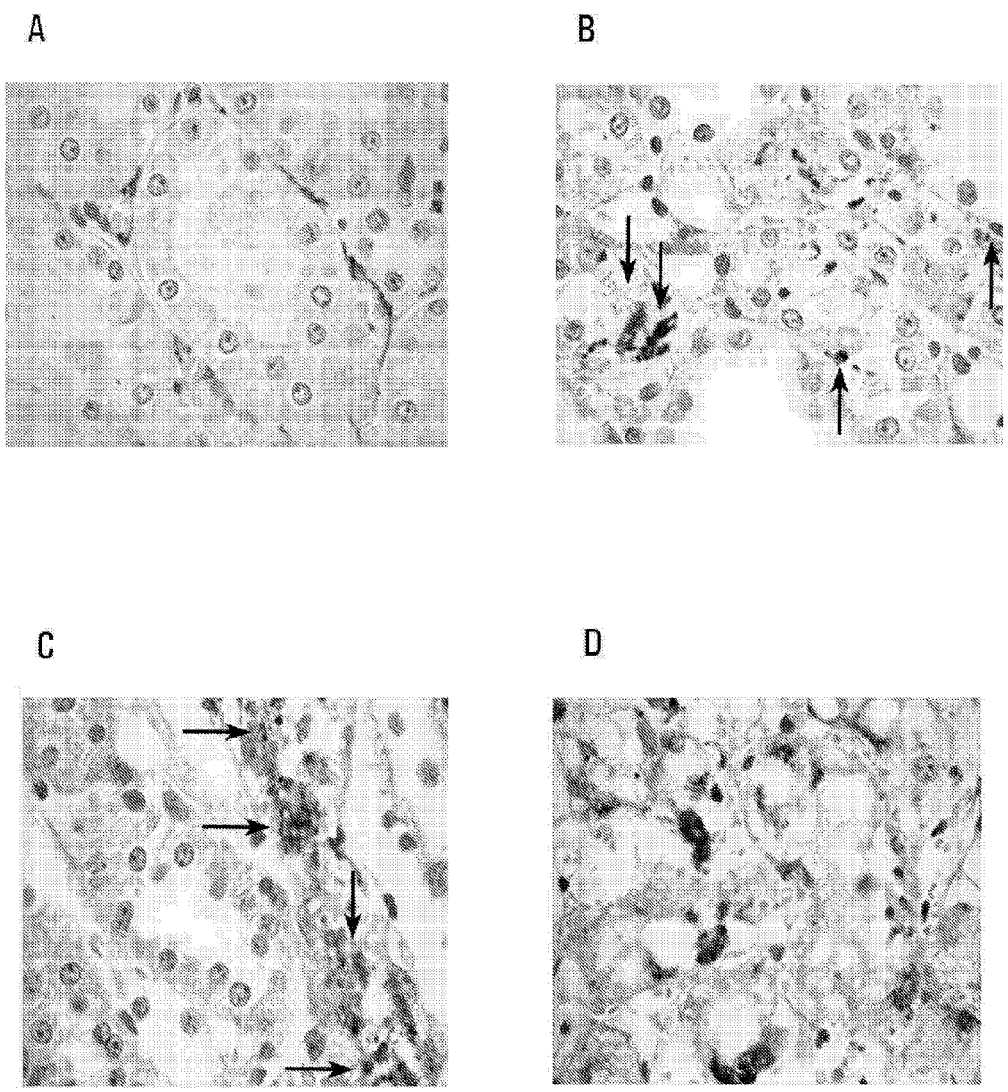
FIG 18A,B,C&D

SEQ ID NO: 1-Gene encoding VCP from strain WR:

```
  1  tttttattat ttgtacgatg tccaggataa cattttttacg gataaataaa tatgaaggtg
 61  gagagcgtga cgttcctgac attgttggga ataggatgcg ttctatcatg ctgtactatt
121  ccgtcacgac ccattaatat gaaatttaag aatagtgtgg agactgatgc taatgctaat
181  tacaacatag gagacactat agaatatcta tgtctacctg gatacagaaa gcaaaaaatg
241  ggacctatat atgctaaatg tacaggtact ggatggacac tctttaatca atgtattaaa
301  cggagatgcc catcgcctcg agatatcgat aatggccaac ttgatattgg tggagtagac
361  tttggctcta gtataacgta ctcttgtaat agcggatatc atttgatcgg tgaatctaaa
421  tcgtattgtg aattaggatc tactggatct atggtatgga atcccgaggc acctatttgt
481  gaatctgtta aatgccaatc ccctccatct atatccaacg gaagacataa cggatacgag
541  gattttata ccgatggcag cgttgtaact tatagttgca atagtggata ttcgttgatt
601  ggtaactctg gtgtcctgtg ttcaggagga gaatggtccg atccacccac gtgtcagatt
661  gttaaatgtc cacatcctac aatatcaaac ggatacttgt ctagcgggtt taaaagatca
721  tactcataca acgacaatgt agactttaag tgcaagtacg gatataaact atctggttcc
781  tcatcatcta cttgctctcc aggaaataca tggaagccgg aacttccaaa atgtgtacgc
```

SEQ ID NO:2-Mature VCP polypeptide (signal sequence removed) from strain WR

```
  1  CCTIPSRPIN MKFKNSVETD ANANYNIGDT IEYLCLPGYR KQKMGPIYAK
 51  CTGTGWTLFN QCIKRRCPSP RDIDNGQLDI GGVDFGSSIT YSCNSGYHLI
101  GESKSYCELG STGSMVWNPE APICESVKCQ SPPSISNGRH NGYEDFYTDG
151  SVVTYSCNSG YSLIGNSGVL CSGGEWSDPP TCQIVKCPHP TISNGYLSSG
201  FKRSYSYNDN VDFKCKYGYK LSGSSSSTCS PGNTWKPELP KCVR
```

FIG 19

SEQ ID NO:3- rVCP E108K polypeptide (substituted amino acid in bold)

```
  1  CCTIPSRPIN MKFKNSVETD ANANYNIGDT IEYLCLPGYR KQKMGPIYAK
 51  CTGTGWTLFN QCIKRRCPSP RDIDNGQLDI GGVDFGSSIT YSCNSGYHLI
101  GESKSYCKLG STGSMVWNPE APICES

SEQ ID NO: 5- rVCP H98Y, E120K polypeptide (substituted amino acid in bold)

```
  1   CCTIPSRPIN  MKFKNSVETD  ANANYNIGDT  IEYLCLPGYR  KQKMGPIYAK
 51   CTGTGWTLFN  QCIKRRCPSP  RDIDNGQLDI  GGVDFGSSIT  YSCNSGYYLI
101   GESKSYCELG  STGSMVWNPK  APICESVKCQ  SPPSISNGRH  NGYEDFYTDG
151   SVVTYSCNSG  YSLIGNSGVL  CSGGEWSDPP  TCQIVKCPHP  TISNGYLSSG
201   FKRSYSYNDN  VDFKCKYGYK  LSGSSSSTCS  PGNTWKPELP  KCVR
```

SEQ ID NO:6- rVCP H98Y, E108K, E120K polypeptide (substituted amino acid in bold)

```
  1   CCTIPSRPIN  MKFKNSVETD  ANANYNIGDT  IEYLCLPGYR  KQKMGPIYAK
 51   CTGTGWTLFN  QCIKRRCPSP  RDIDNGQLDI  GGVDFGSSIT  YSCNSGYYLI
101   GESKSYCKLG  STGSMVWNPK  APICESVKCQ  SPPSISNGRH  NGYEDFYTDG
151   SVVTYSCNSG  YSLIGNSGVL  CSGGEWSDPP  TCQIVKCPHP  TISNGYLSSG
201   FKRSYSYNDN  VDFKCKYGYK  LSGSSSSTCS  PGNTWKPELP  KCVR
```

FIG 21

US 7,749,963 B2

ISOLATED RECOMBINANT VACCINIA VIRUS COMPLEMENT CONTROL PROTEIN (HRVCP) POLYPEPTIDE

BACKGROUND

Complement comprises a group of over 30 soluble and cell surface proteins that represent a major effector arm of the immune system. Although complement is an important component of the immune system, complement-mediated inflammation plays a role in several inflammatory and auto-immune disorders. There is great interest in developing inhibitors of complement for the treatment of autoimmune and inflammatory disease, and also for use in preventing organ rejection in xenotransplantation.

Vaccinia virus complement control protein (VCP) is known to be a strong inhibitor of the classical, lectin and alternative pathways of complement, acting on both C4 and C3. As such, VCP is a promising candidate for use as a complement inhibitor. Although VCP is an inhibitor of complement activation, it would be beneficial to further improve complement inhibition activity of VCP.

VCP is the naturally occurring protein. rVCP is a protein expressed in a yeast/heterologous system and has the same sequence as natural VCP. The humanised recombinant vaccinia virus complement control protein (hrVCP) of the invention has three amino acid changes as described below.

SUMMARY

The presently disclosed subject matter provides, in some embodiments an isolated recombinant vaccinia virus complement control protein (hrVCP) polypeptide. The hrVCP polypeptide comprises in some embodiments a modified amino acid sequence comprising one or more amino acid substitutions to an amino acid sequence as set forth in SEQ ID NO: 2, wherein the hrVCP polypeptide exhibits a complement activation regulatory activity greater than a complement activation regulatory activity of a polypeptide comprising the amino acid sequence as set forth in SEQ ID NO: 2. In some embodiments, the one or more amino acid substitutions are selected from the group consisting of H98Y, E102K, E108K, E120K, and combinations thereof. Further, in some embodiments, the modified amino acid sequence comprises an amino acid sequence selected from the group consisting of SEQ ID NOs: 3, 4, 5, and 6.

In some embodiments of the presently disclosed subject matter, a method of producing an hrVCP polypeptide having enhanced complement activation regulatory activity is provided. In some embodiments, the method comprises providing a vaccinia virus complement control protein (VCP) polypeptide comprising an amino acid sequence as set forth in SEQ ID NO: 2 and substituting one or more amino acids of the VCP polypeptide amino acid sequence to produce an hrVCP polypeptide having enhanced complement activation regulatory activity when compared to a complement activation regulatory activity of the VCP polypeptide.

In some embodiments of the presently disclosed subject matter, a method of reducing or inhibiting activation of complement in a subject is provided. In some embodiments, the method comprises administering to the subject an effective amount of an hrVCP polypeptide.

In some embodiments of the presently disclosed subject matter, a method of treating a disorder in a subject resulting from complement-mediated inflammation is provided. In some embodiments, the method comprises administering to the subject a therapeutically effective amount of an hrVCP polypeptide, or a pharmaceutically acceptable salt thereof.

In some embodiments of the presently disclosed subject matter, a pharmaceutical composition comprising an hrVCP polypeptide and a pharmaceutically acceptable carrier or excipient is provided.

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

DETAILED DESCRIPTION

I. Definitions

Unless otherwise defined, all technical and scientific terms used herein have the same meaning as commonly understood by one of ordinary skill in the art to which the presently disclosed subject matter pertains. For clarity of the present specification, certain definitions are presented hereinbelow.

Following long-standing patent law convention, the terms "a", "an" and "the" mean "one or more" when used in this application, including in the claims. For example, the phrase "a modification" refers to one or more modifications, unless the context in which the phrase appears is clearly to the contrary.

The terms "associated with", "operably linked", and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The terms "coding sequence" and "open reading frame" (ORF) are used interchangeably and refer to a nucleic acid sequence that is transcribed into RNA such as mRNA, rRNA, tRNA, snRNA, sense RNA, or antisense RNA. In some embodiments, the RNA is then translated in vivo or in vitro to produce a polypeptide.

The term "complementary" refers to two nucleotide sequences that comprise antiparallel nucleotide sequences capable of pairing with one another upon formation of hydrogen bonds between the complementary base residues in the antiparallel nucleotide sequences. As is known in the art, the nucleic acid sequences of two complementary strands are the reverse complement of each other when each is viewed in the 5' to 3' direction.

As is also known in the art, two sequences that hybridize to each other under a given set of conditions do not necessarily have to be 100% fully complementary. The terms "fully complementary" and "100% complementary" refer to sequences for which the complementary regions are 100% in Watson-Crick base-pairing, i.e., that no mismatches occur within the complementary regions. However, as is often the case with recombinant molecules (for example, cDNAs) that are cloned into cloning vectors, certain of these molecules can have non-complementary overhangs on either the 5' or 3' ends that result from the cloning event. In such a situation, it is understood that the region of 100% or full complementarity excludes any sequences that are added to the recombinant molecule (typically at the ends) solely as a result of, or to facilitate, the cloning event. Such sequences are, for example, polylinker sequences, linkers with restriction enzyme recognition sites, etc.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant, the promoter can also be specific to a particular tissue, organ, or stage of development.

The term "fragment" refers to a sequence that comprises a subset of another sequence. When used in the context of a nucleic acid or amino acid sequence, the terms "fragment" and "subsequence" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc.

A fragment can also be a "functional fragment", in which the fragment retains a specific biological function of the nucleic acid sequence or amino acid sequence of interest. For example, a functional fragment of a transcription factor can include, but is not limited to, a DNA binding domain, a transactivating domain, or both. Similarly, a functional fragment of a receptor tyrosine kinase includes, but is not limited to a ligand binding domain, a kinase domain, an ATP binding domain, and combinations thereof.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "heterologous", "recombinant", and "exogenous", when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

A "homologous" nucleic acid (or amino acid) sequence is a nucleic acid (or amino acid) sequence naturally associated with a host cell into which it is introduced.

The term "inhibitor" refers to a chemical substance that inactivates or decreases the biological activity of a polypeptide such as a complement component.

The term "isolated", when used in the context of an isolated DNA molecule or an isolated polypeptide, is a DNA molecule or polypeptide that, by the hand of man, exists apart from its native environment and is therefore not a product of nature. An isolated DNA molecule or polypeptide can exist in a purified form or can exist in a non-native environment such as, for example, in a transgenic host cell.

The term "mature polypeptide" refers to a polypeptide from which the transit peptide, signal peptide, and/or propeptide portions have been removed.

The terms "modified amino acid", "modified amino acid sequence", "modified polypeptide", and "modified polypeptide sequence" refer to an amino acid sequence (or a polypeptide comprising that amino acid sequence) that is different from a native amino acid sequence (or a polypeptide that has such an amino acid sequence) that results from an intentional manipulation of the amino acid sequence or the nucleic acid sequence encoding the amino acid sequence. For example, an hrVCP is a modified polypeptide and comprises a modified amino acid sequence because it contains at least one amino acid substitution relative to a naturally occurring VCP amino acid sequence (see e.g., the naturally occurring sequence of VCP set forth in SEQ ID NO: 2 as compared to the modified amino acid sequences presented in SEQ ID NOs: 3-6).

The term "native" refers to a gene that is naturally present in the genome of an untransformed cell. Similarly, when used in the context of a polypeptide, a "native polypeptide" is a polypeptide that is encoded by a native gene of an untransformed cell's genome.

The term "naturally occurring" refers to an object that is found in nature as distinct from being artificially produced by man. For example, a polypeptide or nucleotide sequence that is present in an organism (including a virus) in its natural state, which has not been intentionally modified or isolated by man in the laboratory, is naturally occurring. As such, a polypeptide or nucleotide sequence is considered "non-naturally occurring" if it is encoded by or present within a recombinant molecule, even if the amino acid or nucleic acid sequence is identical to an amino acid or nucleic acid sequence found in nature.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res* 19:5081; Ohtsuka et al. (1985) *J Biol Chem* 260: 2605-2608; Rossolini et al. (1994) *Mol Cell Probes* 8:91-98). The terms "nucleic acid" or "nucleic acid sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long.

A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived.

The term "isolated", when applied to a nucleic acid or polypeptide, denotes that the nucleic acid or polypeptide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A polypeptide that is the predominant species present in a preparation is substantially isolated. The term "isolated" denotes that a nucleic acid or polypeptide gives rise to essentially one band in an electrophoretic gel. Particularly, it means that the nucleic acid or polypeptide is in some embodiments at least about 50% pure, in some embodiments at least about 85% pure, and in some embodiments at least about 99% pure.

The terms "significant increase" or "greater than" refers to an increase in activity (for example, inhibition of complement activation or inhibition of the activity of a complement component) that is larger than the margin of error inherent in the measurement technique. In some embodiments an increase in inhibition by about 10% or greater over a baseline activity (for example, the inhibitory activity of a naturally occurring VCP versus the inhibitory activity of an hrVCP under a given set of conditions), in some embodiments an increase by about 20% or greater, in some embodiments an increase by about 25% or greater, and in some embodiments an increase by about 50% or greater is a significant increase in inhibitory activity.

The terms "significantly less" and "significantly reduced" refer to a result (for example, activation of complement or an activity of a complement component) that is reduced by more than the margin of error inherent in the measurement technique. In some embodiments a decrease in activation or activity by about 10% or greater over a baseline activity (for example, the activation of complement activity or the activity of a complement component in the presence of a naturally occurring VCP versus the same in the presence of an hrVCP under a given set of conditions), in some embodiments a decrease in activation or activity by about 20% or greater, in some embodiments a decrease in activation or activity by about 25% or greater, and in some embodiments a decrease in activation or activity by about 50% or greater is a significantly reduced activation of complement or activity of a complement component.

The term "subsequence" refers to a sequence of nucleic acids or amino acids that comprises a part of a longer sequence of nucleic acids or amino acids (e.g., polypeptide), respectively.

The term "transformation" refers to a process for introducing heterologous DNA into a cell. Transformed cells are understood to encompass not only the end product of a transformation process, but also transgenic progeny thereof.

The terms "transformed", "transgenic", and "recombinant" refer to a cell of a host organism such as a mammal into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof. A "non-transformed," "non-transgenic", or "non-recombinant" host refers to a wild type organism, e.g., a mammal or a cell therefrom, which does not contain the heterologous nucleic acid molecule.

II. Novel Polypeptides and Polynucleotides

Complement forms an important part of the innate immune system. It comprises about 30 proteins, some of which act within a cascade-like reaction sequence, while others serve as control proteins or as cellular receptors. For a review of the complement system, see Walport, M. J. (2001), *N. Eng. J. Med.*, vol. 344, pp. 1058-1066 and Walport, M. J. (2001), *N.*

Eng. J. Med., vol. 344, pp. 1140-1144, herein incorporated by reference. Certain components are present in the blood in precursor forms and must be activated. Complement can be activated by any of three pathways, (1) the antibody-dependent classical pathway (C1-C4-C2-C3), (2) the carbohydrate-dependent lectin pathway (MBL-C4-C2-C3), and (3) the alternative pathway (C3b-Factor B-C3), which is triggered directly by pathogen surfaces.

Activated complement has many functions, including initiation of inflammation, recruitment of leukocytes, clearance of immune complexes, neutralization of pathogens, regulation of antibody responses and cytolysis (the lytic pathway, via C5b-C6-C7-C8-C9, i.e., the membrane attack complex (MAC)). The complement system is a very powerful mediator of inflammation, and complement activation generates proinflammatory peptides such as the anaphylatoxins C3a and C5a, which recruit and activate leukocytes, the cell-bound opsonins C4b and C3b, which facilitate phagocytosis of the target, and MAC, i.e., C5b-9, which lyses target cells and may activate bystander cells to release pro-inflammatory mediators. Uncontrolled activation of complement and consequent host cell damage is prevented by a vast array of regulatory proteins, either circulating in plasma or expressed at the cell surface. However, in some circumstances, control of complement activation is inadequate or absent, which can result in deleterious effects, such as that seen in certain autoimmune and inflammatory diseases.

Vaccinia complement control protein (VCP) is a strong inhibitor of the classical, lectin and alternative pathways of complement, acting on both C4 and C3. VCP is a 35 kDa, soluble, secreted product of the vaccinia virus containing four short consensus repeats that share the greatest sequence homology with several proteins of the regulators of complement activity (RCA) family, including C4 binding protein (C4-bp; 38% identity), membrane cofactor protein (MCP; 35% identity) and decay-accelerating factor (DAF; 31% identity). SEQ ID NO: 1 provides the nucleotide sequence encoding a VCP polypeptide isolated from a vaccinia virus (strain Western Reserve). SEQ ID NO: 2 provides the amino acid sequence of the mature polypeptide (i.e., without the signal sequence) encoded by SEQ ID NO: 1. FIGS. 19, 20 and 21 set out listings of sequences disclosed herein. VCP shares the greatest functional similarity with complement receptor 1 (CR1). VCP binds to C4b, blocks the formation of the classical pathway C3 convertase, binds C3b, causes the accelerated decay of the classical pathway convertase, and blocks the conversion of C3 to C3b in both the classical and alternative pathways by promoting Factor I cleavage of C3b. Like its soluble mammalian RCA counterparts C4-bp and Factor H, but unlike the membrane RCA molecules decay accelerating factor (DAF), membrane cofactor protein (MCP), and soluble complement receptor 1 (CR1), it displays heparin-binding capabilities, suggesting an in vivo role in connection with heparan sulfate proteoglycans lining the endothelial cell layer. By blocking complement activation at multiple sites, VCP downregulates proinflammatory chemotactic factors (C3a, C4a, and C5a) resulting in reduced cellular influx and inflammation.

Further detailed description of VCP can be found in the following references, each of which is incorporated herein by reference: Kotwal, G. J. & Moss, B. (1988) *Nature*, vol. 335(6186), pp. 176-178; Kotwal, G. J. & Moss, B. (1989) *J. Virol.*, vol. 63, pp. 690-696; U.S. Pat. No. 5,157,110; U.S. Pat. No. 5,187,268; Kotwal. G. J. et al. (1990) *Science*, vol. 250 (4982), pp. 827-830; McKenzie, R. et al. (1992) *J. Infect. Dis.*, vol. 166, pp. 1245-1250; Sahu, A. et al. (1998) *J. Immunol.*, vol. 160, pp. 5596-5604; Smith, S. A. et al. (2000) *J. Virol.*, vol. 74, pp. 5659-5666; Murthy, K. H. et al. (2001) *Cell*, vol. 104, pp. 301-311; and Smith, S. A. et al. (2003) *Biochim. Biophys. Acta*, vol. 1650, pp. 30-39. In view of the described functional characteristics of VCP, it is considered to be a promising molecule for inhibiting complement activation and reducing complement-mediated inflammation. However, it would be desirable to further increase the complement activation regulatory activity of VCP.

In some embodiments, the presently disclosed subject matter provides an isolated recombinant vaccinia virus complement control protein (hrVCP) polypeptide. The hrVCP polypeptide comprises in some embodiments a modified amino acid sequence comprising one or more amino acid substitutions to an amino acid sequence of a naturally occurring VCP polypeptide, such as for example the polypeptide sequence as set forth in SEQ ID NO: 2, wherein the hrVCP polypeptide exhibits a complement activation regulatory activity greater than a complement activation regulatory activity of a naturally occurring VCP polypeptide.

Modifications to the naturally occurring VCP polypeptides can be carried out using techniques known in the art, including site-specific mutagenesis. Site-specific mutagenesis (also referred to as "site-directed mutagenesis") is a technique useful in the preparation of individual peptides, or biologically functional equivalent proteins or peptides, through specific mutagenesis of the underlying DNA. The technique further provides a ready ability to prepare and test sequence variants; for example, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is employed, with about 5 to 10 residues on both sides of the junction of the sequence being altered.

In general, the technique of site-specific mutagenesis is well known in the art (see e.g., Adelman et al. (1983) *DNA* 2:183; Sambrook & Russell (2001) *Molecular Cloning: A Laboratory Manual*, Third Edition, Cold Spring Harbor Laboratory Press, Cold Spring Harbor, N.Y.) and can be achieved in a variety of ways generally known to those of skill in the art.

In some embodiments, the one or more amino acid substitutions are selected from the group consisting of H98Y, E102K, E108K, E120K, and combinations thereof. Further, in some embodiments, the modified amino acid sequence comprises an amino acid sequence selected from the group consisting of SEQ ID NOs: 3, 4, 5, and 6.

As discussed above, VCP exhibits complement activation regulatory activity. For example, VCP binds to C4b, blocks the formation of the classical pathway C3 convertase, binds C3b, causes the accelerated decay of the classical pathway convertase, and blocks the conversion of C3 to C3b in both the classical and alternative pathways by promoting Factor I cleavage of C3b. As such, by blocking complement activation at multiple sites, VCP down-regulates proinflammatory chemotactic factors (C3a, C4a, and C5a) resulting in reduced cellular influx and inflammation. Through selected modifications of the amino acid sequence of a VCP, such as for example a VCP having the amino acid sequence set forth in SEQ ID NO:2, the presently disclosed subject matter provides modified recombinant polypeptides (hrVCP) comprising one or more amino acid substitutions (i.e., changing an amino acid at a given position in SEQ ID NO: 2 to a different amino acid) exhibiting enhanced complement activation regulatory activity, as compared to complement activation regulatory activity found in the VCP from which the hrVCP was derived. In some embodiments therefore, the complement activation regulatory activity comprises regulating activation of a classical complement activation pathway, an alternative complement activation pathway, or both the classical and alternative complement activation pathways. Further, in some embodiments, regulating activation of the classical complement activation pathway, the alternative complement activation pathway, or both the classical and alternative complement activation pathways comprises inhibiting activation of at least one complement component, inhibiting activity of at least one activated complement component, or combinations thereof. Further, in some embodiments, the complement component comprises C3 or C4 and the activated complement component comprises C3b or C4b.

Measuring a change in complement activation regulatory activity can be achieved by any of several techniques related to measuring complement activation and activity as are generally well known in the art. For example, activation of the classical complement pathway can be measured using a sensitized sheep red blood cell assay and activation of the alternative complement pathway can be measured using an immunoassay that measures complement factor Bb formation.

The presently disclosed subject matter further provides isolated nucleic acids encoding an hrVCP polypeptide as disclosed herein above.

III. Methods of Producing Recombinant VCP

The presently disclosed subject matter further provides methods of producing an hrVCP polypeptide having enhanced complement activation regulatory activity. In some embodiments, the method comprises providing a naturally occurring VCP polypeptide, such as for example a naturally occurring VCP polypeptide comprising an amino acid sequence as set forth in SEQ ID NO: 2, and substituting one or more amino acids of the VCP polypeptide amino acid sequence to produce an hrVCP polypeptide having enhanced complement activation regulatory activity when compared to a complement activation regulatory activity of the naturally occurring VCP polypeptide. In some embodiments, site-specific mutagenesis is utilized, as discussed in detail herein above, to substitute one or more amino acids of the naturally occurring VCP to produce a novel hrVCP.

IV. Therapeutic Methods and Pharmaceutical Formulations

The presently disclosed subject matter provides methods of reducing or inhibiting activation of complement in a subject. In some embodiments, the methods comprise administering to the subject an effective amount of an rVCP polypeptide.

The presently disclosed subject matter also provides methods of treating a disorder in a subject resulting from complement-mediated inflammation. In some embodiments, the methods comprise administering to the subject a therapeutically effective amount of an hrVCP polypeptide, or a pharmaceutically acceptable salt thereof.

A disorder resulting from complement-mediated inflammation refers to disorders in which complement activation results in undesirable effects in a subject. The complement-mediated inflammation can be a primary cause of the disorder or a mediating factor in the persistence of the disorder. Exemplary complement-mediated inflammation disorders include, but are not limited to, atherosclerosis, rheumatoid arthritis, reperfusion injury, Alzheimer's disease, traumatic brain injury, multiple organ dysfunction syndrome, immune complex disease, spinal cord injury, shock, stent site inflammation, human immunodeficiency virus dementia, macular degeneration, and xenotransplant organ rejection.

Further with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

As used herein, the phrase "therapeutically effective amount" refers to an amount of a therapeutic composition sufficient to produce a measurable response (e.g., a biologically or clinically relevant response in a subject being treated) when administered to a subject. Actual dosage levels of active ingredients in the pharmaceutical compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved.

The potency of a therapeutic composition can vary, and therefore a "therapeutically effective amount" can vary. However, one skilled in the art can readily assess the potency and efficacy of a candidate compound of the presently disclosed subject matter and adjust the therapeutic regimen accordingly. In some embodiments, for example, a therapeutically effective amount of a complement inhibitor for the treatment and/or prophylaxis of atherosclerosis is from about 0.01 g/kg to about 0.1 g/kg per dose.

In some embodiments, the compound is administered orally or parenterally as a pharmaceutical formulation in dosage unit formulations containing standard, well-known non-toxic pharmaceutically acceptable carriers, excipients, adjuvants, and vehicles as desired. The term "parenteral" as used herein includes intravenous, intracerebroventricular, intramuscular, intra-arterial injection, and infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one of skill would know to purify the carrier and therapeutic compound sufficiently to render it essentially free of undesirable contaminants, such as endotoxins and other pyrogens such that it does not cause any untoward reactions in the subject receiving the formulation.

It will be understood that various details of the presently disclosed subject matter may be changed without departing from the scope of the subject matter disclosed herein. Furthermore, the foregoing description is for the purpose of illustration only, and not for the purpose of limitation.

Figure 3:
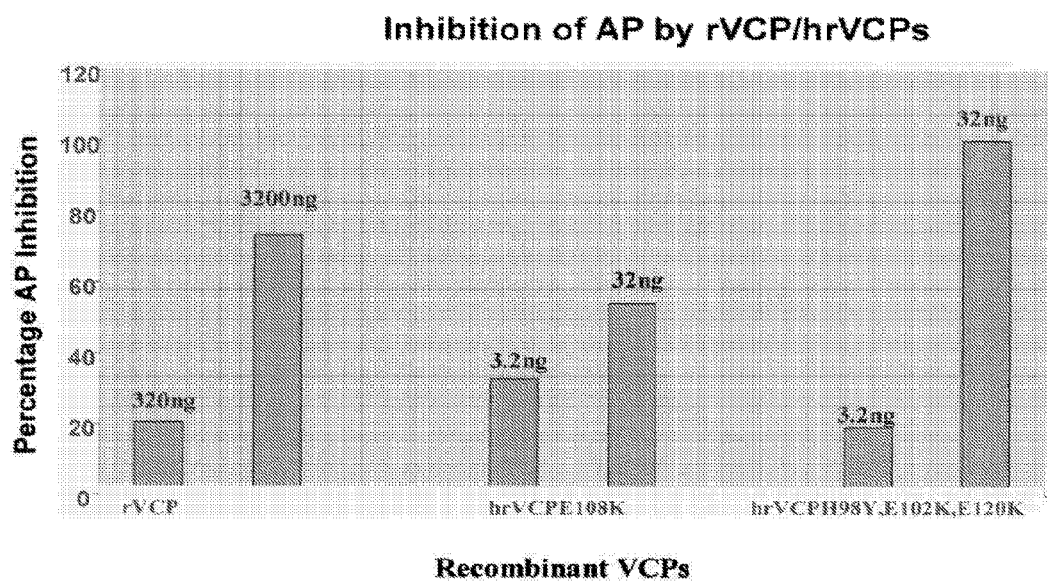
Figure 4:
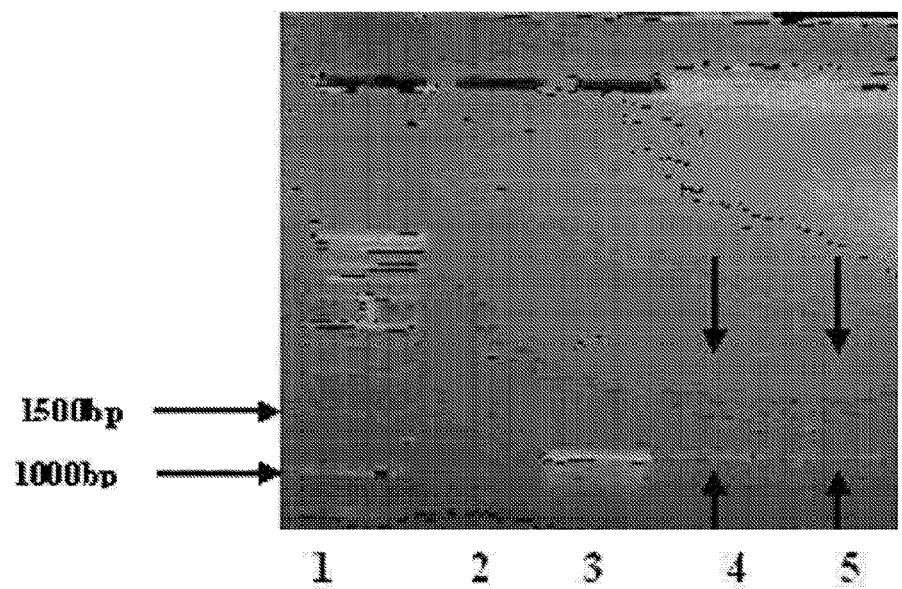

The invention is now described, by way of example, with reference to the following Examples and Figures, in which:

FIG. 1 shows Coomassie blue stained SDS-PAGE (12%) analysis of recombinant VCPs. Lane-1) molecular weight marker; Lane-2) rVCP; Lane-3) $^{hrVCP}$E108K; and Lane-4) $^{hrVCP}$H98Y,E102K,E120K;

FIG. 2A shows inhibition of complement-mediated red cell lysis by rVCP/hrVCPs. The coordinates represent the percentage of inhibition by rVCP (diamonds), $^{hrVCP}$E108K (rectangles) or $^{hrVCP}$H98Y,E102K,E120K (triangles) at the specified amounts. Experiments were performed in duplicates;

FIG. 2B shows a comparison of the potency of rVCP with that of $^{hrVCP}$E108K and $^{hrVCP}$H98Y,E102K,E120K respectively at the indicated amounts. $^{hrVCP}$E108K showing ~25-fold increased potency (ranging 19.7 to 33.7-times), and $^{hrVCP}$H98Y,E102K,E120K displaying ~100-fold increased activity (ranging 91.8 to 116-times) than rVCP in regulating the classical pathway of complement activation. Experiments were performed in duplicates and the error bars represent SD;

FIG. 3 shows a comparison of the potency of rVCP with that of $^{hrVCP}$E108K and $^{hrVCP}$H98Y,E102K, E120K. $^{hrVCP}$E108K (IC$_{50}$ value of 32 ng) showing ~55-fold increased activity and $^{hrVCP}$H98Y,E102K,E120K (IC$_{50}$ value of 16 ng) showing 100-fold increased potency than rVCP (IC$_{50}$ value of 1760 ng) in inhibiting the alternative pathway of complement activation;

FIG. 4 shows Agarose gel electrophoresis (1.2%) of recombinant *Pichia pastoris* yeast genomic DNA performed using AOX-1 universal primers. Lane-1: 1 kb$^+$ MW marker; lane-2: negative (H$_2$O control); lane-3: rVCP/AOX-1 gene control amplified from Ppic9 vector (1222 bp); lanes 4 & 5: hrVCP genes amplified from Ppic9 (1222 bp each). Note: AOX-2 genes (2200 bp) indicated by upper arrows (lanes 4&5).

FIG. 5 A) SDS-PAGE analysis (12%) & B) Western blotting of rVCP (lane-1); $^{hrVCP}$H98Y,E102K,E120K (lane-2) and authentic VCP (lane-3). Lane-M (FIG. 2A) is molecular weight marker.

FIGS. 6A and B show SDS-PAGE analysis of urine samples A) pre (lanes 1 & 3) and post I/R injury (lanes 2 & 4) of VCP treated rat. Pre (lane-5) and post (lane-6) I/R injury of PBS group. B) Standard VCP (28.8 kDa) (lane-1); baseline control from sham 'injured' (lane-2) and sampled at sacrifice (after ~ 8 hours) (lane-3).

Figure 7:
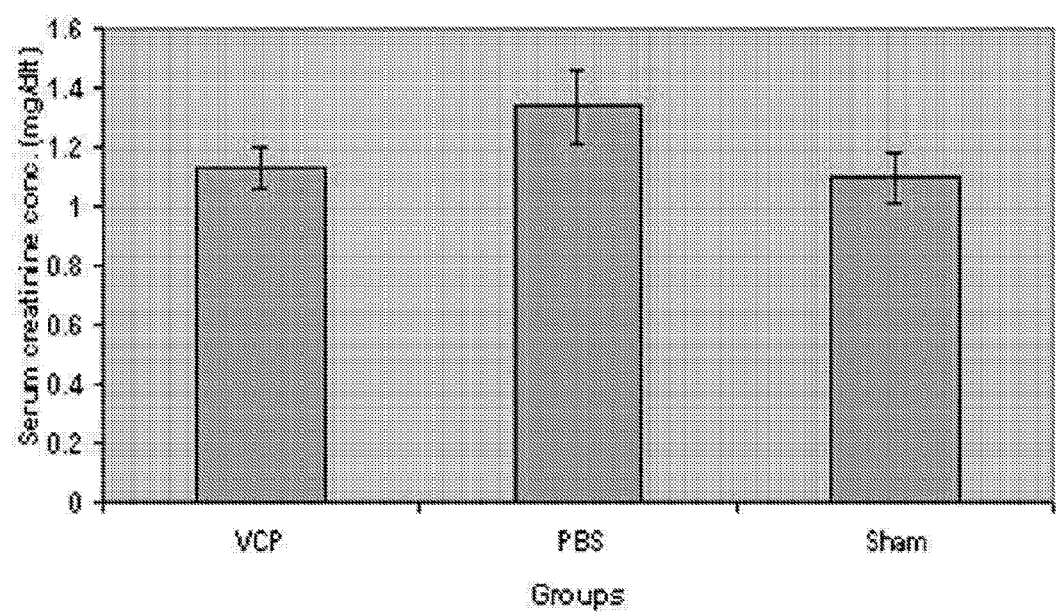

FIG. 7 shows mean serum creatinine concentration 24 hrs after I/R injury. Bars represent standard errors of sample mean (mean±SEM).

FIGS. 8A and B show H & E stained left (A) and right (B) kidney histology displaying normal tubular epithelial cells following sham 'injury' (photographs taken at 40× objective magnification at different contrast of visible light).

FIGS. 9 A and B show H & E stained kidney histology in the VCP treated group demonstrating normal tubular epithelial cell population in the left kidney (A) and focal necrosis (arrows) of tubular epithelial cells (B) following 24-hours ischemia/reperfusion injury (40× objective magnification FIGS. 10 A, B and C show H & E stained kidney histology in the PBS vehicle control group portraying normal tubular epithelial cell population in the left kidney (A) and extensive tubular epithelial cell necrosis in the right renal cortex (B). C) shows cortico-medullary (arrows) necrosis following 24-hours ischemia/reperfusion injury. All, except C) at 10×, were at 40× objective magnification.

FIGS. 11 A, B and C show H & E stained right kidney histology: A) normal tubular epithelial cells (sham group); B) focal necrosis (arrows) of tubular epithelial cells (VCP group) and C) extensive tubular epithelial cell necrosis (renal cortex) (PBS group). (40× objective magnification).

FIG. 12 A and B show immunostaining for VCP showing A) strong tubular epithelium stain (arrows) and B) negatively stained section (Sham group). Magnification at 40×.

FIGS. 13 A, B and C show immunostaining for C3: A) focal deposition in the tubular epithelium of the VCP group (arrows) & B) markedly elevated deposition in the renal tubules of the PBS group. C) shows basal staining between the epithelium. Magnification at 40×.

Figure 14:
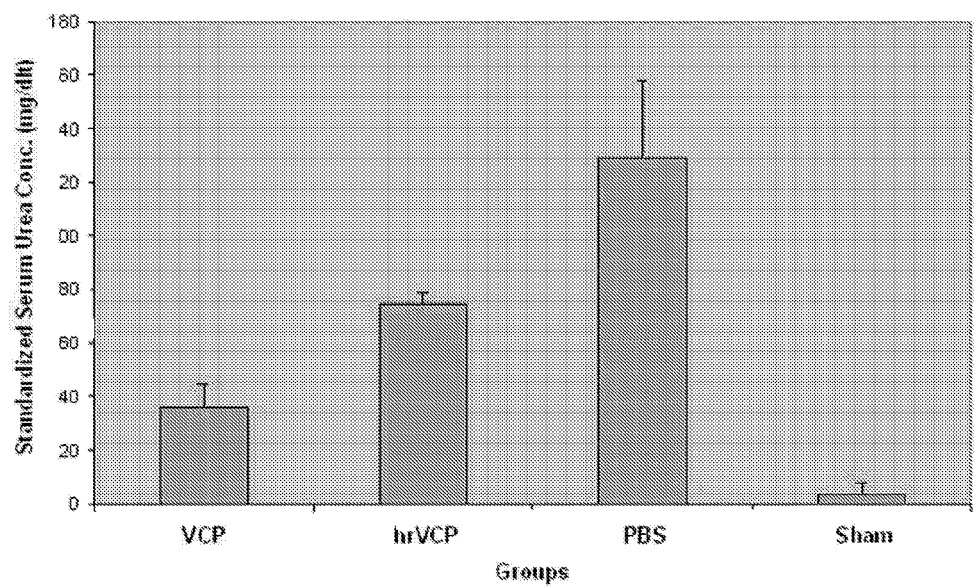

FIG. 14 shows mean serum urea concentration following 24 hours bilateral I/R injury (Note: a 3.7-fold and 1.73-fold rise in the PBS group compared to the VCP and the hrVCP treatment groups respectively. The Sham group showed almost intact urea concentrations. Bars represent standard errors of sample mean (mean±SEM).

Figure 15:
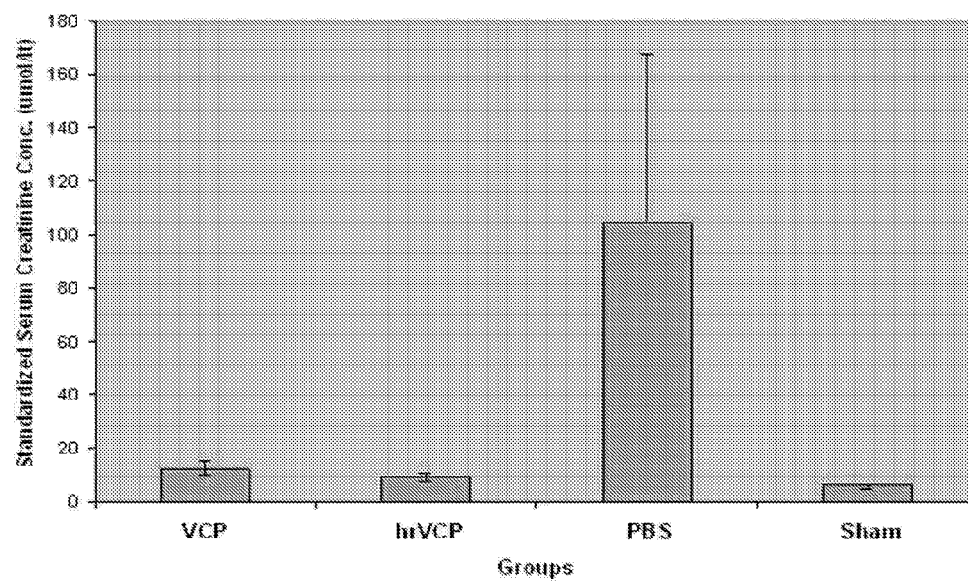

FIG. 15 shows mean serum creatinine concentration after 24 hours Ischemia/Reperfusion (I/R) injury (Note: ~8.5-fold and 11.6-fold increase in the PBS group compared to the VCP and the hrVCP treatment groups respectively. The sham group showed normal creatinine concentration. Bars represent standard errors of sample mean (mean±SEM).

Figure 16:
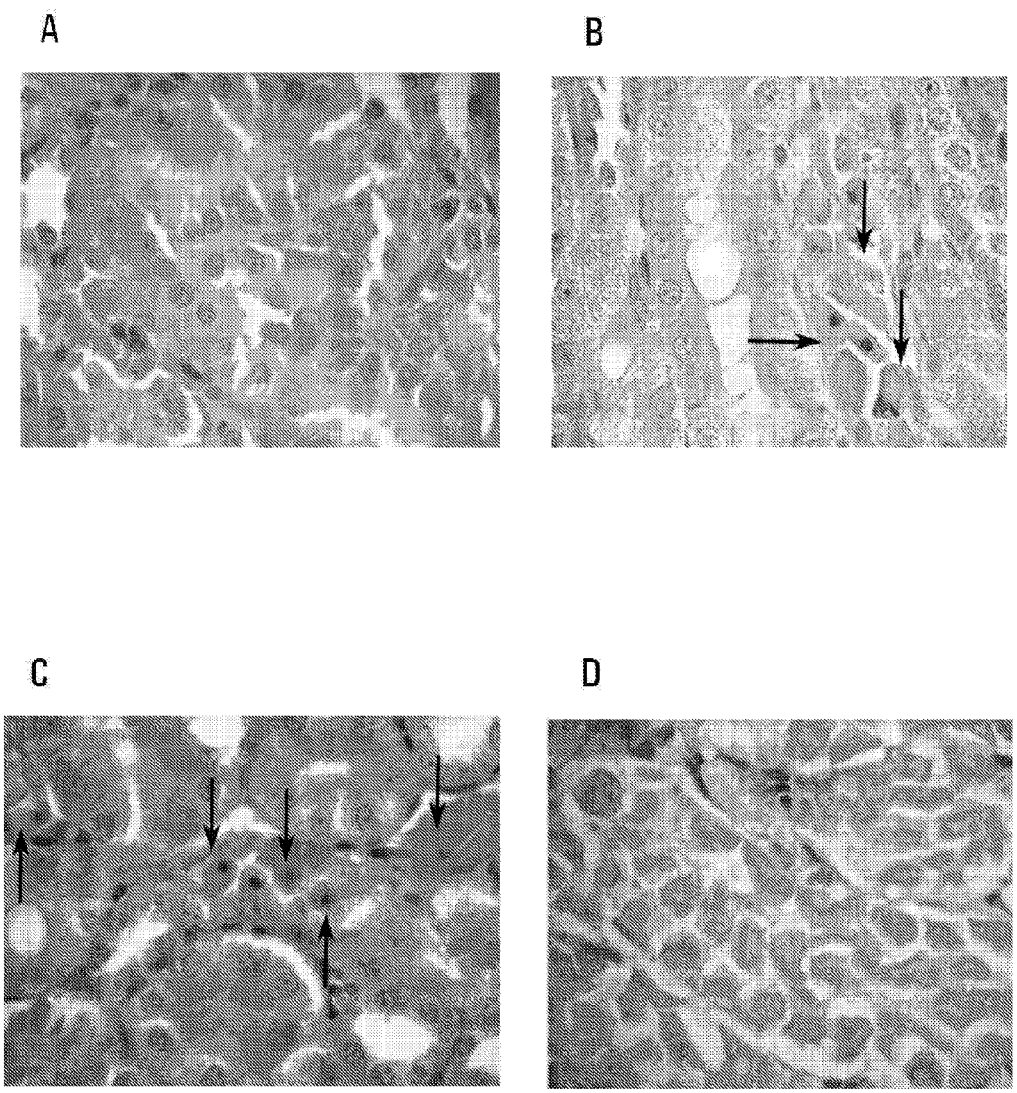

FIGS. 16A, B C and D show H & E stained renal histology showing A) normal tubular epithelial cells following sham 'injury', B) focal necrosis (arrows) of tubular epithelial cells following authentic VCP treatment, C) focal necrosis (arrows) of tubular epithelial cells following recombinant VCP (hrVCP) treatment and D) diffuse necrosis of tubular epithelial cells in the PBS group following 24-hours ischemia/reperfusion (I/R) injury. (Representative fields of the Sham, VCP, hrVCP and the PBS group are shown) (40× objective magnification).

Figure 17:
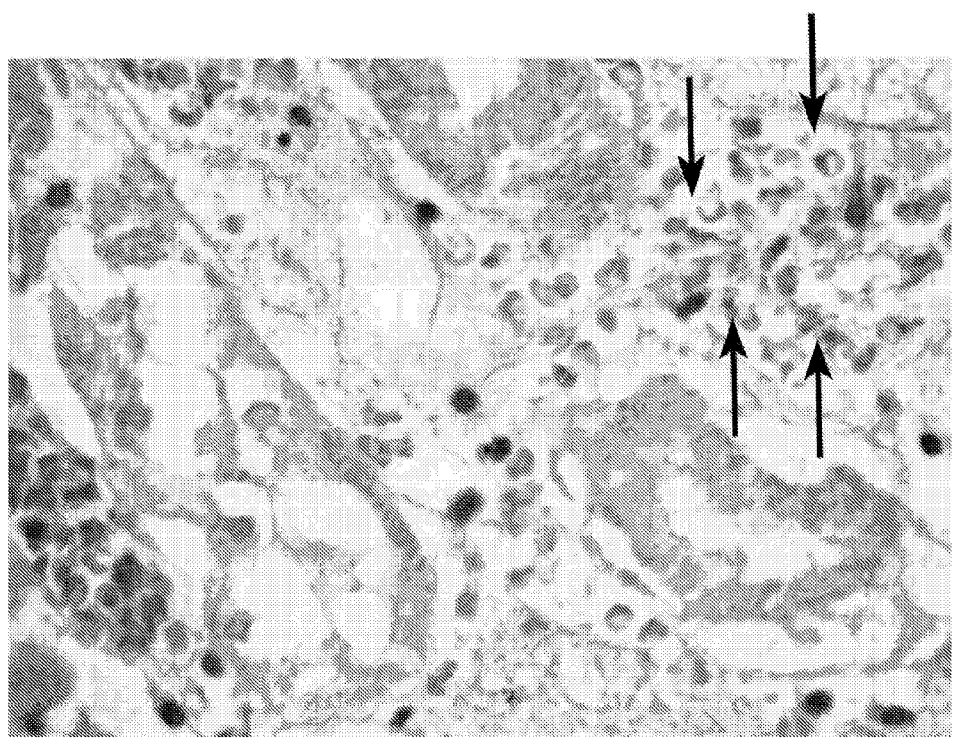

FIG. 17 shows H & E staining showing recruitment of inflammatory cells (neutrophils) following renal I/R injury in the PBS group (arrows) (40× objective magnification).

FIGS. 18A, B C and D show immunostaining for complement component C3: A) basal staining between the epithelia in the sham group; B) minimal deposition in the tubules of the authentic VCP treatment group (arrow), C) focal deposition in the tubules of the recombinant VCP (hrVCP) treatment group (arrows) D) markedly elevated C3 deposition in the renal tubules of the PBS group. (40× objective magnification)

FIG. 19 shows SEQ ID NO 1 and 2.
FIG. 20 shows SEQ ID NO 3 and 4.
FIG. 21 shows SEQ ID NO 5 and 6.

EXAMPLE 1

Materials & Methods

Cloning of rVCP/hrVCP

Genomic DNA was isolated from the Western Reserve (WR) strain of vaccinia virus, and degenerate set of primers were designed to amplify the ORF of VCP while introducing 5' EcoRI and 3' NotI sites. The mutagenesis experiments were based on the native crystal structure, molecular modeling and sequence alignment with other complement control proteins in the databank.

The amplicons were cloned into the expression vector pPIC9, downstream of an alcohol oxidase promoter, and GS115 *Pichia pastoris* yeast cells were transfected using the spheroplasting technique (Invitrogen life technologies). The cells putative to express pPIC9 integrated inserts were screened by PCR using the AOX-1 universal primers (Invitrogen life technologies) and the recombinant clones were used for subsequent expression studies.

Expression of rVCP/hrVCP

Expression of the recombinant proteins was performed by inoculating single colonies into 400 ml of buffered minimal glycerol medium (BMGY) at 30° C. at 200 rpm until the $OD_{600}$ reached between 2 and 6. The cells were harvested and resuspended in 100 ml of buffered minimal methanol medium (BMMY) containing 4% methanol under similar conditions for 96 hrs, and the samples were SDS-PAGE analysed.

Samples expressing a band at the size of the standard VCP were filter sterilized (Adcock Ingram filter units), diluted in binding buffer (50 mM sodium acetate, pH 5.5) and passed through a 5 ml HiTrap heparin column (Millipore) preequilibrated with the same binding buffer. The protein was then eluted with a linear NaCl gradient of 0 to 100% at a flow rate of 1 ml/min. The fractions containing pure rVCP/hrVCP were tested for biological activity using hemolysis assay for the classical pathway and using Bb fragment enzyme immunoassay for the alternative complement pathway.

Regulation of the Classical Complement Pathway

This assay is based on antigen-antibody complex and subsequent complement activation and quantitates the classical complement pathway and terminal complement components. The activities of rVCP and the humanized recombinant VCPs (hrVCPs) were determined by testing their ability to inhibit complement-mediated lysis of sensitised sheep red blood cells (ssRBCs) (Diamedix Corporation). Samples containing equal amounts of the different proteins were tested at different concentrations (FIG. 2A) and their activities compared (FIGS. 2A & B). Standard human serum was used as a source of complement and was activated by incubating at 37° C. with the IgG-sensitized sheep red cells. After 1 h incubation, the samples were centrifuged at 7000 rpm for 30 seconds and the supernatants analysed for the extent of lysis by measuring absorbance at 405 nm.

Regulation of the Alternative Complement Pathway

This enzymatic immunoassay selectively quantitates the degree of the alternative complement pathway activation. This assay measures the amount of the generated proteolytic enzyme Bb, a cleavage product of the alternative pathway specific factor B zymogen, activated in the presence of C3b and the alternative pathway enzyme factor D. Although, the kit seems to have been developed for the assessment of naturally activated alternative complement components due to microbial infections or autoimmunity, we modified the procedure by pre-activating the alternative pathway in a standard human serum using the yeast cell derived zymosan (Sigma-Aldrich).

Undiluted standard human serum was first mixed with different amounts of rVCP, $^{rVCP}$E108K or $^{rVCP}$H98Y,E102K, E120K and then with 12.5 μg of pre-sonicated (2×30 sec) zymosan and incubated at 37° C. for 1 h. The samples were centrifuged at 3700 rpm for 2 min to remove any pelleted zymosan particles. Serum sample alone and serum with equivalent amounts of zymosan in the absence of rVCP/hrVCPs were used as negative and positive controls respectively. All the samples were diluted to a final concentration of 1/10 with complement specimen diluent before use. The samples (100 μl each) were added into pre-washed eight-well microplate assay strips immobilized with mouse anti-human Bb monoclonal antibody (Quidel Corporation) and incubated for 30 min at room temperature. The bound Bb was detected by adding 50 μl of horseradish peroxidase (HRP)-conjugated goat anti-human Bb antibody and developed by adding the 1/20 diluted chromogenic substrate. The concentration of Bb fragment was measured at 405 nm and the potency of rVCP was compared with the hrVCPs (FIG. 3).

Results

Based on X-ray crystallographic structure, computer modeling exercises and sequence alignment with its variola virus homolog, SPICE, and its host homologs CR1 and MCP, putative C3b/C4b binding sites have been mapped on rVCP. Using site-directed mutagenesis studies, we generated the single mutant $^{rVCP}$E108K to make the residue identical to that of SPICE, and the triple mutant $^{rVCP}$H98Y,E102K,E120K based on the sequence alignment with SPICE and MCP (H98Y), modeling studies (E102K) and alignment with CR1 and SPICE (E120K).

The recombinant proteins were purified and SDS-PAGE analysed as shown in FIG. 1. The purity of the proteins was comparable, the band intensities were measured, and the concentrations estimated using the Biorad microplate assay protocol (Biorad).

The biological activity of the different recombinant proteins was then compared for both the classical and the alternative complement pathways in a series of dilutions. Compared to the rVCP, the single mutant $^{rVCP}$E108K showed nearly 25-fold more in inhibiting the classical pathway (FIG. 2B) and nearly 55-fold more potency in inhibiting the alternative complement pathway with an $IC_{50}$ value of 32 ng (FIG. 3). The triple mutant $^{rVCP}$H98Y,E102K,E120K revealed almost 100-fold increased potency in inhibiting both the classical complement pathway with an $IC_{50}$ value of 50 ng and the zymosan-induced alternative complement pathway with an $IC_{50}$ value of 16 ng compared to the rVCP with an $IC_{50}$ value of 1760 ng in inhibiting the latter pathway (FIG. 3). This suggests that the deduced amino acids truly interact with C3b/C4b and enable the humanized rVCPs (hrVCPs) to effectively block complement activation. The values of the inhibitory concentrations at 50% ($IC_{50}$) suggest that the triple mutant $^{rVCP}$H98Y,E102K,E120K possess ~3-fold more potency in inhibiting the alternative pathway than the classical pathway. None of the amino acid substitutions are in the previously described heparin-binding region of rVCP. Furthermore, the purification studies indicate that the heparin binding affinity is intact.

In fact, the residue change at position 102 (E102K) has created an additional putative heparin binding site of the K-X-K type and has increased the number of putative heparin binding sites from one to two in this module (SCR-2) and from four to five in the entire protein. Therefore, the generated recombinant protein may have rendered in vivo biological advantages such as controlling the aggregation of inflammatory cells such as neutrophils & natural killer (NK) cells and increasingly maintaining in vivo retention in the heparan sulfate granules of endothelial cells.

EXAMPLE 2

Materials & Methods

Expression of Recombinant VCP ($^{hrVCP}$H98Y,E102K, E120K)

The PCR-based mutagenesis and cloning of the humanized recombinant VCP (hrVCP) in the Pichia pastoris yeast expression system has been described. The expression of two alcohol oxidase genes (AOX-1 and AOX-2) allows the recombinant yeast clone to metabolize methanol faster (Mut$^+$) than the mere AOX-1 expressing clones (Mut$^s$) upon induction with methanol.

Screening of Recombinant Clones

Selective plates such as the minimal methanol histidine (MMH) medium are often used to screen for putative yeast transformants. However, they do not differentiate the actual recombinants from those harboring the Ppic9 vector without the gene of interest. Therefore, they usually need to be confirmed by PCR. The putative recombinant clones were screened using the forward (5'-GACTGGTTCCAATTGACAAGC-3') and the reverse (5'-GCAAATGGCATTCTGACATCC-3') AOX-1 universal primers (Invitrogen life technologies) and the amplified products were analysed in a 1.2% agarose gel (FIG. 4). The $^{hrVCP}$H98Y,E102K,E120K gene-expressing recombinant clones were used for subsequent protein production experiments.

The recombinant protein was expressed by inoculating positively identified colonies into 30 ml of buffered minimal glycerol complex medium (BMGY) at 30° C. at 200 rpm for 48 hours and then further inoculated into 970 ml of BMGY until the OD$_{600}$ read above 2. The cells were harvested by centrifugation at 4000 g for 4 minutes, rinsed twice with distilled water and resuspended in 250 ml of buffered minimal methanol complex medium (BMMY) containing HPLC grade methanol at a final concentration of 4% for 96 hours.

The samples were SDS-PAGE analysed and those expressing a band at the size of the standard recombinant VCP (rVCP) were purified using a series of HiTrap heparin columns (Ghebremariam et al, 2005). The purified fractions were then SDS-PAGE (12%) analysed (FIG. 5A) and confirmed by Western blotting as described below.

Western Blot

The purified authentic VCP and the hrVCP were SDS-PAGE analysed and confirmed by western blotting (FIG. 5B). The resolved samples were transferred from the gel into an Immobilon-P (PVDF) membrane with a pore size of 0.45 µm (Millipore Corporation, Bedford, Mass.) at a constant current of 0.14 A for 1.3 hours. The membrane was then removed and stained with Ponceau S stain for 1-2 minutes in order to assess the success of the transfer. The membrane was rinsed with TBS prior to blocking with freshly prepared 5% blocking solution at 4° C. overnight. The blocking solution was discarded and the membrane was incubated with 1:1,000 diluted rabbit anti-VCP primary antibody (Vector Laboratories, Burlingame, Calif.) for 1 hour at room temperature with continuous shaking at a rate of 100 revs/min (Orbital Shaker SO3, Stuart Scientific, United Kingdom). The membrane was washed with 30 ml of 0.1% TBS-T twice for 10 minutes each. The membrane was washed again with 30 ml of 0.5% blocking solution twice for 10 minutes each and incubated with 1:12,500 diluted anti-mouse/anti-rabbit IgG peroxidase secondary antibody (Roche Diagnostics, Mannheim, Germany) for 30 minutes with continuous shaking. The membrane was then rinsed and washed with TBS-T (30 ml each) four times (15 minutes each). The bands were detected by adding premixed detection reagent for 60 seconds. Finally, the blot was inserted into a film cassette and exposed for various time points and the X-ray film was processed by transferring it into a Developer (~2 minutes), Stopper (2% acetic acid) (quick dip) and a Fixer (~2 minutes).

Tissue Culture Experiments

Production of VCP from Natural Infection

The authentic VCP was produced by infecting African green monkey kidney (BSC-1) cells at a titer of 3×10$^6$ cells with the laboratory adapted vaccinia virus vGK5 strain (Kotwal and Abrahams, 2004) at a multiplicity of infection (MOI) of 1 in a serum-free minimal essential medium (MEM) Earle's Base (Highveld Biological, Lyndhurst, South Africa) containing 1× triple antibiotics (Penicillin, Streptomycin and Fungizone, Highveld Biological) for 48 hours.

Production and Passaging of BSC-1 Cells

Pre-produced stock of African green monkey kidney (BSC-1) cell line was generously provided by Prof. Girish J. Kotwal (Division of Medical Virology, UCT) for further cell line production & maintenance experiments.

The cells (~10$^7$) were inoculated into 20 ml of MEM containing 10% fetal calf serum (FCS) (Highveld Biological, Lyndhurst, South Africa) and 1× triple antibiotics (as above) in a 75 cm$^2$ pyrogen free sterile cell culture flask (Corning Incorporated, NY, USA) and incubated at 37° C. in a Thermocyt incubator with 5% CO$_2$ (ESI-Flufrance, Wissous, France). At day four, the cells were fully confluent as revealed under 40× Olympus CK2 light microscope (Japan). Thereafter, the entire medium was aspirated, leaving the adhered cells behind, and the cells were treated (1 minute) with trypsin/EDTA in order to remove any traces of anti-trypsin prior to partial trypsinization with 2 ml of fresh beef pancreas derived gamma irradiated Trypsin/EDTA (Highveld Biological, Lyndhurst, South Africa) at 37° C. with occasional vigorous shaking for 5 minutes. All the cells were detached with the application of gentle mechanical force and in-and-out aspiration as confirmed under a microscope. The cells were resuspended in 10 ml of fresh MEM and transferred into 15 ml tube for centrifugation at 100 g at 20° C. for 5 minutes (Heraeus Multifuge 3 L-R, Kendro Laboratory Products, Hanau, Germany). Finally, the supernatant was discarded and the cell pellet was resuspended in 0.5 ml of cryoprotective medium (basal eagle's medium containing Hanks' BSS & 15% DMSO) (BioWhittaker, Walkersville, Md.). The cell-suspension was aliquoted into 2 ml cryovials and stored at −80° C. and the cells were thawed and passaged when necessary.

Virus Titration

The BSC-1 cells (0.5 ml×6) were plated out in 6-well plates (Corning Incorporated, NY, USA) until confluency (~72 hours) and each well, except the negative control, was infected with the pre-titrated vaccinia virus vGK5 strain (initial stock kindly provided by Walter Rangel De Campos, MSc graduate) at a titer range of $10^6$-$10^{10}$ plague forming units (pfu) per ml as follows:

The original stock ($2 \times 10^7$ pfu/ml) was diluted by mixing 1 μl of the virus with 1 ml of fresh MEM (without FCS and antibiotics). A μl of the mix was added to the well labeled as $10^6$, mixed, and 100 μl of this mix was transferred into the well labeled as $10^7$ and so on up to the $10^{10}$ labeled well. The cells were infected by incubating them with the different viral titers' at 37° C. for 48 hours. The supernatant was removed and the wells were stained with crystal violet stain. Subsequently, the number of plaques was counted and the viral titer was determined.

Confirmation of Infectivity and Virus Production

To confirm the infectivity of the newly produced vGK5 strain, confluent 6-well plate grown BSC-1 cells were infected with vGK5 virus at a multiplicity of infection (MOI) of 0.1 by adding 1.5 μl of virus stock ($3 \times 10^4$ viral particles) into $3 \times 10^6$ cells in 1 ml. After 24 hours of infection, the entire medium was sucked out and the cells were resuspended in 1 ml of serum free MEM and incubated further at 37° C. for 24 hours. After a total of 48 hours of infection, the supernatants were harvested and the wells were stained with crystal violet for 1 hour at room temperature. Once the infective ability of the virus was confirmed, virus stocks were produced by infecting fully confluent BSC-1 cells with a viral titer of $2 \times 10^8$ pfu/ml for 48 hours. The cell monolayer was washed twice with 0.5 ml of PBS (pH 7.2) and the cells were detached using a cell scraper. The cell suspension was harvested and freeze-thawed between −80° C. and 37° C. three times followed by sonication using an ultra sonic cell disrupter (Vir-Tis, NY, USA) for 30 seconds in ice. The supernatant (viral particles) was clarified by centrifuging at 4000 g for 5 minutes and the viral particles were aliquated in eppendorf tubes & stored at −80° C. for further use The post-infection supernatant containing secreted VCP was purified from the supernatant under similar conditions to the $^{hrVCP}$H98Y,E102K,E120K containing supernatant as described above. The fractions containing pure VCP and $^{hrVCP}$H98Y,E102K,E120K were pooled and dialysed against distilled water. The protein concentration was estimated using the BioRad assay as described below. The dialysed protein was lyophilized and resuspended in phosphate buffered-saline (PBS; pH 7.2). The final protein was then monitored for bacterial endotoxins using the QCL-1000 Chromogenic Limulus Amebocyte Lysate (LAL) quantitative assay (BioWhittaker, Walkersville, Md.) prior to biological use.

Estimation of Protein Concentration

The concentration of the purified proteins was estimated using the bovine serum albumin (BSA) standards (Pierce Laboratories) and the Bio-Rad DC protein assay reagents in a 96-well micro plate assay. This colorimetric assay is based on the principle of the Lowry assay and involves the initial reaction of the protein (standard or sample) with the supplied alkaline cooper tartrate solution (reagent A). This reduction reaction ($Cu^{2+}$ to $Cu^+$) further reacts with specific amino acids constituting the protein and upon the addition of Folin reagent (reagent B), blue color, equivalent to the protein concentration, develops and this can be measured spectrophotometrically or using a microplate reader.

Five μl of the samples or standard was mixed with 25 μl of the supplied reagent A, mixed well & then 200 μl of reagent B was added into each well. The mixture was incubated at room temperature for 5 minutes and the protein concentration was measured at 595 nm using microplate reader.

Screening for Endotoxin

Bacterial endotoxins are usually active contaminants of genomic DNA, plasmid and proteins in solutions. These toxins also known as lipopolysaccharides (LPSs) are often derived from gram-negative bacteria. Vaccines or any other therapeutic materials need to be monitored for endotoxins prior to their in vivo use as they may cause septic shock, hypotension and multiple organ dysfunction syndrome. The Chromogenic Limulus Amebocyte Lysate (LAL) test is a widely used enzymatic assay for the quantification of endotoxins and applies the catalysis of a proenzyme into its active form by bacterial endotoxins resulting to the development of a yellow color proportional to the concentration of endotoxin present in the sample (BioWhittaker Manual). In this experiment, the microplate assay method (BioWhittaker Manual) was used. Initially, a 96-well plate and all the reagents were pre-warmed at 37° C. Fifty μl of blank (endotoxin free water), standard or sample was added into each well and then 50 μl of the supplied LAL was added into each well and mixed prior to 10 minutes incubation at room temperature. The supplied substrate solution (100 μl) preheated to 37° C. was added into each well, mixed and incubated for 6 minutes at 37° C. The reaction was then stopped by adding 100 μl of stop reagent (10% SDS) and the endotoxin concentration was measured at 405 nm using a microplate reader.

In Vitro Complement Inhibition

The biological ability of VCP and $^{hrVCP}$H98Y,E102K, E120K to inhibit the classical and/or the alternative complement pathway(s) was evaluated in 96-well based in vitro assays.

Serum Assay

This assay demonstrates the ability of a given serum to lyse 95% of sensitized sheep red blood cells (ssRBCs). Because not every individual has the same level of circulating complement, the amount of serum responsible to lyse 95% ssRBCs need to be determined when using sera from different sources and even when using serum from the same source stored for an extended period of time. In this experiment, three sterile eppendorf tubes were labeled as 1:30, 1:60 or 1:90, and 75 μl of ssRBCs suspension was added into each tube. Ten μl of the supplied gelatin-veronal-buffer (GVB) was added into each tube and mixed well. Normal human serum was thawed from −80° C. and diluted 1:30, 1:60 or 1:90. Fifteen μl of each dilution was added into the respective tube and the samples were incubated at 37° C. for 1 hour prior to centrifugation at 7000 rpm for 30 seconds. Finally, 75 μl of each sample was transferred into a well in a 96-well plate. The absorbance, proportional to the percentage of lysis, was measured at 405 nm measurement filter and the dilution that yielded 95% lysis was used for the subsequent hemolysis assay as illustrated below.

Inhibition of the Classical Complement Pathway

The abilities of VCP and $^{hrVCP}$H98Y,E102K,E120K to block complement mediated lysis of sheep red cells (Diamedix Corporation, Miami, USA) were tested by preincubating the IgG-sensitized red cells with the respective protein and activating the antigen-antibody dependent classical pathway using human serum as a source of complement as demonstrated earlier.

In this experiment, 75 μl of sensitized sheep red blood cells (ssRBCs) suspended in gelatin-veronal-buffer (GVB) were transferred into clean eppendorf tubes and then different amounts of each protein (20-100 ng) were added to the respectively labeled tubes. Finally 15 μl of 1:60 diluted human serum (determined using serum assay as described above) was added into each tube except the negative control. The samples were incubated at 37° C. for 1 hour, centrifuged at 7000 rpm for 30 seconds and 75 μl of the supernatant was transferred into each well of a 96-well plate. The absorbance, proportional to the percentage of lysis, was measured at 405 nm and was subtracted from 100% to calculate the percentage of inhibition. The result was standardized in the background of the negative control in order to account the complement independent spontaneous lysis of the cells.

Inhibition of the Alternative Complement Pathway

The $^{hrVCP}$H98Y,E102K,E120K was evaluated for its ability to inhibit the alternative complement pathway by measuring a cleavage product of an alternative pathway specific enzyme, Bb (Quidel Corporation) as described previously. Briefly, the alternative complement pathway was selectively activated using zymosan, a component of the yeast cell wall. The humanized recombinant protein was preincubated with human serum and the mix was then incubated with 12.5 μg of double-sonicated zymosan at 37° C. for 1 hour. Subsequently, 10 μl of each mix was transferred into clean eppendorf tubes and 90 μl of the supplied complement specimen diluent (Quidel Corporation) was added in order to make 1:10 dilution. Prior to the addition of samples, each well in the 8-well strip was washed with 200 μl of 1× wash buffer three times (1 minute each). The samples (100 μl each) were added into the pre-washed wells coated with mouse anti-human Bb antibody and incubated for 30 minutes at room temperature in order to allow the capture of the generated Bb fragments by the monoclonal antibody. The samples were then discarded and the wells were washed 5× using a multi-channel pipetter (1 minute per wash). Horseradish peroxidase (HRP)-coupled goat anti-human Bb (50 μl) was added and incubated for 30 minutes to detect the bound Bb. The conjugate was then discarded and each well was washed 5× as described above. The color was developed by adding 100 μl freshly prepared substrate solution and incubated at room temperature for 30 minutes. Finally, 50 μl stop solution (contains 250 mM oxalic acid as described in the insert provided) was added to stop the reaction and the absorbance of the developed color, equivalent to the concentration of Bb fragment, was measured at 405 nm measurement filter. In this experiment, naïve serum and serum sample preincubated with equivalent amount of zymosan (in the absence of the protein) were used as negative and positive controls respectively. The kit is normally used to assess the activation of Factor B in patients' sera. Here for the first time, the protocol has been adapted to evaluate the ability of a complement inhibitor to regulate the alternative complement pathway by selectively activating the alternative pathway in normal human serum.

Animal Experiments

Procedure-1

Four male long Evans rats weighing 147-157 g were used in this study. The animals were caged under standard conditions including a regular light and dark cycle with unlimited access to rat chow and water prior to the start of the experiment. The research protocol was approved by the University of Cape Town animal research ethics committee.

Ischemia/Reperfusion Injury

The animals were anesthetized with a combination of diethyl ether inhalation and ketamine hydrochloride (100 mg/kg, im). The abdomen was cleaned with a cleaning solution and shaved with surgical blade. Laparotomy was performed by midline incision and both kidneys were dissected. The animals were catheterized and baseline blood and urine were collected prior to ischemia. Ischemic damage was induced by clamping both the right and left renal arteries (bilateral clamping) with non-traumatic vascular clamps for 45 minutes. The flow of blood was reestablished by removing the clamps and the abdominal cavity was closed with 4-0 prolene blue monofilament polypropylene suture (Ethicon, PA). In addition to the baseline, blood samples were collected at reperfusion and every 2 hours after the reestablishment of blood flow until sacrifice, blood and urine samples were collected for urea and creatinine studies (serum) and for SDS-PAGE analysis (urine). Both kidneys were harvested and fixed in 10% formalin for histopathological studies.

Administration of rVCP

In the VCP recipient group, the recombinant VCP (rVCP) was administered both intravenously (IV) and intraperitoneally (IP) in one animal. In order to potentially prevent or at least minimize ischemia, an IP injection of 25 mg/kg was administered two hours before the laparotomy. Moreover, an IP injection of 30 mg/kg was given just after closing the abdominal wall. Furthermore, 15 minutes before clamping, a bolus IV dose of 8 mg/kg was administered through the femoral vein. Subsequently, rVCP was administered IV (1.5 mg/kg) 15 minutes before releasing the clamps (that is 30 minutes after applying the clamps), just after removing the clamps and every 15 minutes for 2 hours hoping to prevent or at least minimize reperfusion injury.

In order to comparatively choose the most suitable route of administration and possibly cut the tedious and engaging IV administration, rVCP was administered (n=1) only IP in the same interval and at the same dosage to the IP route of the first animal. Blood and urine samples were collected at the same intervals. In one animal, phosphate buffered-saline (PBS, pH=7.2) was administered both IV and IP at equivalent intervals to the administration of rVCP in the first animal. In this procedure, one animal was included as a sham control in order to understand the effects of anesthesia and surgical procedure induced stress in the blood biochemistry. In this animal, the kidneys were similarly isolated, however, no clamps were applied and the animal did not receive any injection.

Blood Urea Nitrogen (BUN) Assay

The blood samples were allowed to clot at room temperature overnight. The serum was separated by centrifuging at 3000 rpm for 25 minutes and kept at −20° C. until use. The samples were thawed once prior to the biochemical study. Here, the Kinetic UV method was used to measure the serum BUN levels. One reagent tablet was first dissolved in 1 ml of supplied buffer (Boehringer, Mannheim). After 15 minutes, 10 μl of serum or standard (precinorm U at 50 mg/dl) was added to every ml of the solution and mixed gently. Finally, two absorbances were taken at 340 nm at 30 seconds ($A_1$) and 3 minutes ($A_2$) after the addition of the sample or standard and the concentration of urea was calculated as:

$$C(mg/dl) = \frac{A_1 - A_2}{B_1 - B_2} \times 50$$

Where $A_1$ & $A_2$ are sample and $B_1$ & $B_2$ are standard absorbance at 30 seconds and 3 minutes respectively Creatinine Assay The blood samples were separated as described above in the BUN assay and 50 μl of each serum was diluted (1:1) with distilled water. Two hundred μl of sodium tungstate was added and mixed well. Thereafter, 200 µl of sulphuric acid was added, mixed and centrifuged at 3000 rpm for 15 minutes.

Following the spinning, 200 µl of each supernatant was transferred into a clean eppendorf tube and was mixed with 200 µl of picric acid. Finally, 200 µl of NaOH (0.75 M) was added and incubated for 20 minutes at room temperature. The absorbance was taken at 520 nm.

This experiment was done using the HiTachi U-2000 spectrophotometer and two standards and a positive control with known creatinine concentration were used to justify and calculate the concentration of creatinine in the sample.

The creatinine concentration was calculated as follows;

$$C(mg/dl) = \frac{\text{Sample absorbance}}{\text{Standard absorbance}^*}$$

*The "standard absorbance" was the averaged result of two independant absorbances.

Urinalysis

In order to confirm the previously suggested hypothesis of the rapid exclusion of VCP from circulation and to clarify the presence of high molecular weight proteins following ischemia/reperfusion injury, urine samples (baseline and sacrifice) were comparatively elucidated via SDS-PAGE. The samples were kept at 4° C. and then 20 µl of each sample was transferred into clean eppendorf tubes and centrifuged at 7000 rpm for 5 minutes. The supernatant was separated and 16.5 µl was mixed with 6.5 µl of loading buffer mix and then evaluated by SDS-PAGE.

Procedure-2

Seven male Long Evans rats weighing 240-274 g were used in the study. The animals were housed under standard temperature and pressure (STP) including a regular light and dark cycle with free access to rat chow and water 24 hours prior to the procedure and then free access to water for the duration of the experiment.

Ischemia/Reperfusion Injury

The animals were initially anesthetized with a combination of diethyl ether inhalation and ketamine hydrochloride (100 mg/kg, im) (Centaur Labs). The abdominal region was cleaned with a surgical detergent and laparotomy was performed by midline incision.

With the exception of the sham control, acute renal failure was induced by removal of the right kidney (right nephrectomy) followed by 45 minutes occlusion of the left renal pedicle (artery & vein). In this procedure, the animals were allowed to stabilize following the nephrectomy prior to the contralateral clamping. The perfusion of blood was reestablished by removing the vascular clamps and the abdominal cavity was closed with silk black-braided 5-0 Sharpoint precut suture (Sharpoint, USA). In addition to the baseline, blood samples were collected at the time of reperfusion, and then every 2 hours until sacrifice or the completion of the experiment. The right kidney (trimmed for identification) was prefixed in 10% formalin and the left kidney was harvested during sacrifice and fixed likewise.

Administration of rVCP

The recombinant VCP (rVCP) was administered both intravenously (IV) and intraperotoneally (IP) in two of the rVCP recipients. A bolus dose of 8 mg/kg was injected IV (through the renal vein), 60 minutes before applying the clamps and 30 minutes after clamping (although the renal vein was still clamped during this administration, the first blood that flows following reperfusion was expected to immediately transport the protein and contribute to prevent reperfusion injury).

An IP dose of 30 mg/kg was administered 2 hours before the start of the experiment, just after the establishment of blood perfusion and then every 4 hours until sacrifice or the completion of the experiment. In two vehicle control animals, normal saline (0.9%) (Adcock Ingram, Johannesburg, RSA) was administered both IV and IP at equivalent intervals to the administration of rVCP.

Moreover, in order to observe the effect of a non-complement inhibitor protein on ischemia/reperfusion injury, one animal was administered (IV & IP) with bovine serum albumin (BSA) at equivalent intervals to the administration of rVCP and normal saline. BSA was chosen due to the easier availability of the protein.

In addition to the aforementioned control animals, one animal was used as a nephrectomy control without contralateral clamping. It was expected to draw lessons on the ability of a single intact kidney to clear metabolic wastes, the degree of stress and discomfort triggered by nephrectomy, and most importantly to evaluate the effect of proteins; complement inhibitor and non-inhibitor, in renal ischemia/reperfusion injury. A sham control was also included to understand the effect of anesthesia and the possible stress created by lengthy operations. In this animal, a similar surgical procedure was followed to dissect the kidneys.

However, neither nephrectomy nor clamping was applied and the animal did not receive any injection during the course of the study. The body temperature of the animals was maintained by covering them with a regulated warming blanket.

Blood Urea Nitrogen (BUN) Assay

The blood samples were allowed to clot at room temperature for 2 hours and the serum was separated by spinning at 300 rpm for 25 minutes and stored at −20° C. until use. In this biochemical experiment, the Kinetic UV method was used to quantify the concentration of urea in the serum samples. This method applies the breakdown of the urea in the sample into ammonium ($NH_4^+$) by the help of the catalytic enzyme urease and then the generated $NH_4^+$ undergoes an oxidation reaction with alpha-ketoglutarate and the coenzyme nicotinamide adenine dinucleotide (NADH) in the presence of glutamate dehydrogenase (GLDH) to yield glutamate and $NAD^+$ which is proportional to the concentration of urea in the sample.

The chemical reaction is displayed as follows:

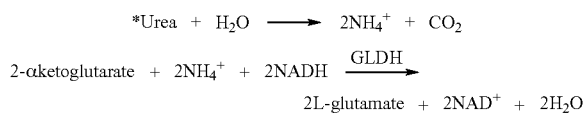

* The chemical representation of the reaction reproduced from the MPR2 Urea Kinetic UV method supplied insert (Boehringer, Mannheim).

The amount of sample used, time of incubation and absorbance measurement filter was similar to the one explained under procedure-1 above.

Creatinine Assay

The same batch of serum (to the ones used for BUN assay) and all other required solutions as well as the amount of sample used, time of incubation, standards and absorbance measurement filter described above for the creatinine assay were used in this set of experiment.

Histopathological Study

Both kidneys of each rat were sectioned longitudinally and then fixed, dehydrated, cleared, wax impregnated and embedded in paraffin. The sections were cut in 1-2 μm sections and stained with Hematoxylin and Eosin (H & E) stain. A blinded expert evaluated the sections.

Procedure-3

Six male Long Evans rats weighing 156-176 g were used in this study. The animals were caged under standard conditions including a regular light (12-hour) and dark (12-hour) cycle with free access to rat food and water prior to the experiment. The animals were diet restricted from the day before the procedure.

Ischemia/Reperfusion Injury

The animals were anesthetized with a combination of ether inhalation and ketamine hydrochloride (100 mg/kg, im). The abdominal area was sterilized with a cleaning solution and was shaved to expose the abdominal skin. Laparotomy was performed by midline incision and both kidneys were isolated. The animals were randomly allocated to receive rVCP, normal saline or sham controls (n=2 each). Baseline blood was collected prior to the induction of ischemia, which was provoked by ceasing the flow of blood in both the right and left renal arteries for 45 minutes. The flow of blood was reestablished by removing the clamps and the abdominal cavity (skin and muscle layer) was closed with 4-0 and 6-0 prolene blue monofilament polypropylene suture. The animals were then stabilized and returned to their cages. In the sham group, both the kidneys were dissected similarly without the application of clamps. Blood samples were collected 8 hourly for 24 hours and the kidneys were harvested for histopathological study.

Administration of rVCP

To further elucidate other potential route of rVCP administration, the rVCP was injected subcutaneously (SC) at 30 mg/kg 2 hours before the surgical procedure and then every 4 hours for the duration of the study period. Normal saline (0.9%) was administered to the (saline) control animals at equivalent intervals to the administration of rVCP. No injection was given to the sham group during the study period.

Blood Urea Nitrogen (BUN) Assay

The BUN assay was performed as described above.

Analysis of Serum Complement

In order to evaluate the efficacy of rVCP administration SC and the expected subsequent complement inhibition, the level of circulating complement was semi-quantified indirectly by hemolysis assay. First, the dilution of serum necessary to lyse 95% of the sensitized sheep red blood cells (ssRBCs) was determined by serum assay as described above. Once the serum dilution was determined, 75 μl of the ssRBCs were mixed with 10 μl of the supplied GVB buffer and 15 μl of serum from the rVCP, saline or sham control rats collected after 24 hours. In the presence of classical complement inhibitors such as VCP the level of complement is expected to be minimal and therefore less of the ssRBCs should be lysed. The reaction mix was incubated at 37° C. for 1 hour and then spun at 7000 rpm for 30 seconds. Seventy-five μl of each sample was transferred into a 96-well microplate. The absorbance was measured at 405 nm and the percentage of lysis, proportional to the level of complement, was calculated and compared between the groups. Here, 75 μl of ssRBCs were incubated without serum as a negative control and human serum at a dilution known to lyse 95% of ssRBCs was used as a positive control.

Histopathological Study

The kidneys were sectioned longitudinally and then fixed in 10% formalin, dehydrated, cleared, wax impregnated and embedded in paraffin. The sections were cut in 1-2 μm sections on a sliding microtome (Leica Microtome sliding 2000R), floated onto microscopic slides and stained with Hematoxylin and Eosin (H & E) stain as briefly described below.

Procedure-4

Nineteen male Long Evans rats weighing 345-418 g were used in the study. The animals were housed under standard temperature and pressure (STP) including a regular light and dark cycle with free access to rat chow and water.

Ischemia/Reperfusion Injury

The animals were anesthetized with ketamine hydrochloride (100 mg/kg, im). The abdominal cavity was cleaned with plasmalyte B cleaning solution and shaved with gamma radiation sterilized surgical blade (Paramount Surgimed Ltd). Laparotomy was performed by midline incision and the right kidney was dissected under surgical microscope. Baseline blood was collected from the inferior vena cava and ischemia was induced by clamping the right renal artery with non-traumatic microvascular clamps for 60 minutes. The perfusion of blood was reestablished by removing the clamp, and the abdominal wall was closed with 4-0 prolene blue monofilament polypropylene continuous suture (Ethicon, PA). The animals were randomly allocated to receive VCP or PBS (n=6 each). Similarly, in the sham group (n=6), the right kidney was dissected, however, no clamp was applied. One animal was exposed to bilateral clamping and no injection was given throughout the study period. At the end of the 24 hours experiment, the animals were overanesthetized and blood was collected from the aorta for biochemical studies. Moreover, the kidneys (left and right) were harvested for histopathological and immunohistochemical studies.

Administration of VCP/$^{hrVCP}$H98Y,E102K,E120K

In the VCP recipient group rats, a combination of the natural infection derived authentic VCP and the newly characterized recombinant VCP ($^{hrVCP}$H98Y,E102K,E120K) was administered both intravenously (IV) and intraperitoneally (IP). Two hours before the laparotomy, an IP injection of 3 mg/kg was given. Subsequently, 5 minutes before clamping, 15 minutes before and 5 minutes after releasing the clamps, an IV dose of 600 μg/kg was administered through the dorsal vein. To maintain the bioavailability of the protein in circulation, an amount of 3 mg/kg was given IP every 4 hours until the completion of the study.

The control group received similar volumes of PBS at equivalent intervals to the administration of VCP/$^{hrVCP}$H98Y, E102K,E120K. The sham group did not receive any injection during the entire study period.

Blood Urea Nitrogen (BUN) Assay

Despite its susceptibility to exogenous factors such as protein-rich diet in one extreme and starvation on the other, the BUN is routinely analysed to assess renal function. In this experiment, the serum levels of urea from the baseline and following the I/R injury were compared. Blood samples were allowed to clot for 45 minutes at room temperature and were centrifuged at 2500 rpm for 30 minutes.

The concentration of urea was estimated using the Urease-UV Kinetic enzymatic assay kit (Kat Medical, Gauteng, South Africa) following the procedure inserted (Kat Medical).

Creatinine Assay

Serum samples obtained using the procedure described above were analysed for creatinine concentration (Merck Chemicals, Gauteng, South Africa) using the HiTachi U-2000 spectrophotometer (HiTachi, Japan) and the mean concentration was compared among the groups (FIG. 7).

Histopathological Study

The harvested kidneys were sectioned longitudinally before they were fixed in 10% formalin (prepared in PBS). The sections were then processed (dehydrated, cleared and wax impregnated; Leica TP 1020 processor, Nussloch, Germany), embedded in paraffin wax, and cut in 1-2 μm sections on a sliding microtome (Leica Microtome sliding 2000R). The sections were floated onto glass slides and heat fixed at 55° C. prior to Hematoxylin and Eosin (H & E) stain. The tissues were initially cleared in xylol for 3 minutes and then twice for 1 minute each prior to dehydration in a series of absolute, 96%, 70% alcohol for 1 minute each. The sections were rinsed with tap water for 1 minute and then hematoxylin stained for 9 minutes. The sections were then rinsed in running tap water for 1 minute and dipped in acid alcohol for 10 seconds prior rinsing with Scott's blue water for 1 minute & in running tap water for another minute. The sections were counterstained with eosin (1%) for 2 minutes and rinsed before dehydrating them in 70%, 96% and absolute alcohol respectively. The sections were finally cleared with xylol and covered with Canada balsam cover slip prior to examination. The histology was interpreted by a pathologist blinded to the treatment that the animals received and the degree of injury was scored (FIG. 11).

Immunohistochemical Study

The paraffin embedded tissue sections (mounted on APES coated slides) were immunostained for VCP and the complement component C3. For the VCP staining (FIG. 12), the sections were heat fixed at 60° C. for about 1 hour prior to dewaxing in xylol for 20 minutes (4 changes, 5 minutes each) and then rehydrated from absolute alcohol to 96% (2 changes, 2 minutes each) and quick rinsed in PBS. Afterwards, the tissue's own (endogenous) peroxidase activity was inhibited using 0.6% commercially available $H_2O_2$, diluted in distilled water, for 5 minutes and then quick rinsed in PBS. Thereafter, both the pressure cooker and the proteolytic enzyme antigen retrieval methods were tried. In the pressure cooker method, the citrate buffer (pH 6.0) was initially boiled and the slides were immersed in the buffer. The cooker was switched on and the boiling pressure was maintained for 2 minutes to 'cook' the tissue before releasing the pressure by the process of conduction. Alternatively, in the proteolytic enzyme antigen retrieval method, the slides were treated with the supplied ready-to-use proteolytic enzyme (DakoCytomation, Denmark) for 8 minutes. The slides were transferred to running tap water for 10 minutes and then rinsed in PBS-(Tween 20) for 5 minutes. The sections were blocked with 1:20 diluted normal goat serum (DakoCytomation, Denmark) for 10 minutes and then incubated with chicken anti-VCP primary antibody (1:150) at 4° C. overnight. For the negative controls, no primary antibody was added. The slides were rinsed with PBS-T for 10 minutes prior to 50 minutes incubation with 1:350 diluted goat anti-chicken secondary antibody (Vector Laboratories, Burlingame, Calif.). The slides were quick rinsed with PBS-T and then incubated for 30 minutes with 1:400 diluted avidin (Dako A/S, Denmark) and rinsed again with PBS-T prior to 5 minutes incubation with the chromogenic substrate 3,3'-diaminobenzidine (DAB) (Novocastra) and then rinsed with PBS and water before enhancing the color with 1% copper sulphate solution for 5 minutes.

The sections were counter stained with hematoxylin for 30 seconds and then treated with BlueScott's water for 30 seconds. Finally, the slides were rinsed with tap water for 5 minutes, dehydrated (in a series of 70%, 96% and absolute alcohol), xylol cleared and then mounted in Entellan (Marienfeld, Germany). The specificity and the degree of antibody staining were interpreted by a pathologist and scored semi-quantitatively.

Complement Component C3 Staining

For the complement staining, APES coated slides were used. The sections were xylol dewaxed and rehydrated prior to treatment with protease (5 mg/ml) at 37° C. for 30 minutes. The slides were rinsed with PBS for 5 minutes and then blocked for endogenous peroxidase activity using 0.3% $H_2O_2$ for 10 minutes and then rinsed in tap water and PBS sequentially. The tissues were blocked with 1:3 diluted normal sheep serum for 20 minutes. Afterwards, the serum was drained off and the slides were incubated with 1:700 diluted rabbit anti-human polyclonal C3 antibody (Dako A/S, Denmark) for 45 minutes and then washed with PBS for 5 minutes prior to incubation with 1:160 diluted swine anti-rabbit peroxidase conjugated secondary antibody. The slides were washed with PBS for 10 minutes and then the color was developed for 2 minutes using DAB. The slides were rinsed and the color was enhanced with copper sulphate solution (1%) for 5 minutes followed by a brief wash with distilled water and counterstaining with Mayers Hematoxylin for 30 seconds. Finally, the sections were treated with BlueScott's water for 30 seconds and then dehydrated, cleared and mounted for immunohistochemical examination. Here, the uninjured (left) kidney of each group mounted on the same slide was used as a background control and the intensity of C3 staining in the right kidneys were compared among the different groups (FIG. 13). Rabbit anti-human polyclonal antibody (Dako A/S, Denmark) with good cross-reactivity to rat C3 was used as a primary antibody and the staining was performed in the department of anatomical pathology, UCT.

Statistical Analysis

The creatinine concentration results are demonstrated as mean±SEM of n independent experiments.

Procedure-5

Fourteen male Long Evans (LE) rats weighing 422-479 g were used in this study. The animals were housed under standard conditions (temperature, pressure and humidity) including a regular light (12-hour) and dark cycle (12-hour) with free access to rat chow and distilled water.

Ischemia/Reperfusion Injury

Based on the various invasive approaches applied to establish ischemia/reperfusion induced acute renal failure, the optimization procedure was finally refined in my own hands. In order to stimulate an ischemia model with both structural and functional feasibility, the following procedure was applied in this experiment.

The animals were anesthetized with forane (isoflurane) inhalation (Abbott Laboratories S.A. (pty) Ltd) and the abdominal cavity was cleaned with a cleaning solution. The abdominal skin was exposed and laparotomy was performed by midline incision. Both kidneys were carefully dissected under surgical microscope and baseline blood was collected from the inferior vena cava. Acute renal failure was triggered by ceasing the flow of blood in both right and left arteries for 60 minutes followed by 24 hours reperfusion. The abdominal cavity was closed with 3-0 ethilon blue monofilament polyamide 6 non-boilable continuous suture (Ethicon, Johnson&Johnson, PA). The animals were allowed to recover after the surgical procedure and were administered with 100 µl of the analgesic drug temgesic (300 µg/ml) (Schering-Plough Ltd, R & C Pharmaceuticals, UK) intramuscularly (IM), to minimize the degree of pain and discomfort provoked by the procedure. The renal failure was induced in both the VCP and $^{hrVCP}$H98Y,E102K,E120K recipients (n=3 each) and the PBS vehicle control groups (n=4). In the sham group (n=4), both the kidneys were similarly isolated without the application of vascular clamps. After 24 hours, the animals were overanesthetized and blood was collected from the aorta for BUN and creatinine studies. The kidneys were harvested for histopathological and immunohistochemical studies.

Administration of VCP/$^{hrVCP}$H98Y,E102K,E120K

Based on the promising therapeutic role of these proteins, we decided to elucidate the therapeutic potential of each protein independently. Three animals received the yeast-cell expressed humanized recombinant VCP, with three critical amino acid difference to the rVCP, ($^{hrVCP}$H98Y,E102K, E120K) and other three animals were administered with the mammalian cell derived authentic VCP. On the basis of the previous partial protection outcomes, higher doses of the proteins (to assess whether the amount of protein administered was a limiting factor) was administered both intravenously (IV) and intra-peritoneally (IP). Two hours before the laparotomy, an IP dose of 4 mg/kg was administered initially. To effectively knock down the level of complement, an IV (dorsal vein) dose of 1 mg/kg was then injected 5 minutes before applying the clamps, 45 minutes after clamping and 5 minutes after releasing the clamps. Due to its slow absorption and hence relatively delayed elimination from the body, the IP dose was given sparingly every 4 hours for the 24 hours study period. The vehicle control group received the same volumes of PBS at equivalent intervals to the administration of VCP. The sham group did not receive any injection during the study period.

Blood Urea Nitrogen (BUN) Assay

The serum urea nitrogen concentration was comparatively estimated between the baseline level and following the I/R injury. The blood samples were allowed to clot for 2 hours at room temperature and the sera was separated by centrifugation at 3000 g for 30 minutes. This enzymatic assay was performed using the Urease-UV Kinetic kit following the procedure provided as described above.

Creatinine Assay

The serum creatinine concentration was estimated using the procedure described above and was repeated in an independent laboratory (The National Health Laboratory Service (NHLS), Clinical Pathology laboratory, Groote Schuur Hospital, UCT) using an automated technique.

Histopathological Study

This study was performed using the protocol adapted from Marilyn Tyler's adapted protocol. The formalin (10%) fixed kidney tissues were dehydrated by immersing them in an increasing percentage of ethanol, xylol cleared and wax impregnated; Leica TP 120 processor, Nussloch, Germany). The tissues were then embedded in liquefied paraffin wax (55-60° C.), and cut in 1-2 µm sections on a sliding microtome (Leica Microtome sliding 2000R).

The sections were mounted onto microscopic slides and heat fixed at 55° C. incubator. The H & E staining protocol was as demonstrated under procedure-4 above. The histology was examined and interpreted by a pathologist blinded to the treatment that the animals received and the degree of injury was semi-quantitatively scored.

Immunohistochemical Study

To assess the density and distribution of the administered VCP and the complement component C3, the paraffin embedded tissue sections mounted on APES coated slides were immunostained as described under procedure-4 above. In this experiment, only the proteolytic enzyme antigen retrieval method was used for the VCP staining. The specificity, degree and the distribution of antibody staining was interpreted by a blinded pathologist and graded semi-quantitatively.

Statistical Analysis

The BUN and creatinine concentration results are demonstrated as mean±SEM of n independent experiments. The values were subjected to one-way analysis of variance (ANOVA) followed by Gosset's 'Student's' t-test.

TABLE 1

Summary of the I/R injury techniques employed in the different procedures described above

| Procedure | Ischemia induced by | Duration of Ischemia (min) | Remarks |
|---|---|---|---|
| 1 | Bilateral clamping | 45 | Animals too small, multiple bleeding caused dehydration and rapid deterioration of their well-being. Animals did not survive for 24 hrs |
| 2 | Right nephrectomy followed by left clamping | 45 | Animals were under continuous anesthesia and lying on the OR table for prolonged period of time. Animals did not survive for 24 hrs. BSA did not have any protective role. |
| 3 | Bilateral clamping | 45 | rVCP administered subcutaneously (SC) did not inhibit the level of circulating complement as confirmed by hemolysis assay |
| 4 | Unilateral clamping | 60 | The VCP/hrVCP combination delivered both IV and IP has reduced renal I/R injury. No significant differences in the serum BUN and Creatinine probably due to the compensatory effect of the contralateral kidney. |

TABLE 1-continued

Summary of the I/R injury techniques employed in the different procedures described above

| Procedure | Ischemia induced by | Duration of Ischemia (min) | Remarks |
|---|---|---|---|
| 5 | Bilateral clamping | 60 | The VCP/hrVCP treated animals showed clinically significant structural and functional integrity compared to the PBS group |

Results

Procedure-1

Serum Creatinine and BUN

Due to the smaller number of animals used in this experiment, the short survival of the animals, and the extreme fluctuation in the biochemical data analysed, there was statistically insignificant (extremely high standard error values) levels of BUN and creatinine within and among the groups. Therefore, the serum urea and creatinine concentration results were rejected based on the null hypothesis.

Urinalysis

The urine samples obtained through catheterization from the baseline and the sacrifice times were SDS-PAGE (12%) analysed to assess the filtration capacity of the renal system for large proteins that could otherwise had been reabsorbed under physiological conditions. Despite the short survival (reperfusion injury) there was significant excretion of bulky proteins following the ischemia/reperfusion injury suggesting early pathological changes in the renal system of the animals exposed to I/R injury. The intensity of the post-reperfusion sample in the PBS vehicle control group looks slightly dense (FIG. 6A, lane-6) compared to the VCP treated animals (FIG. 6A, lanes 2& 4) suggesting the therapeutic value of VCP. Interestingly, the post-reperfusion urine sample in the sham group also displayed significantly brighter banding patterns (FIG. 6B, lane-3) compared to the baseline protein bands (FIG. 6B lane-2) suggesting the possible ischemic damage due to stress, anesthesia and dehydration induced hypovolemic shock.

Procedure-2

Serum Creatinine and BUN

The animals were left lying on the operation (OR) table for the duration of the experiment or until they died. This caused significant swelling in the extremities due to insufficient circulation. In addition, the animals were frequently bled for biochemical studies. Consequently, the rVCP treated, one (of two) PBS control, the nephrectomy control and even the sham control animals died between 5 hours 35 minutes and 17 hours 30 minutes. Neither the BUN nor the serum creatinine levels had significantly deviated from the baseline values in these animals.

One of the saline group animals survived for 23 hours post reperfusion and therefore the BUN 18.68 mg/dlt baseline in the saline group to 192.40 mg/dlt at sacrifice suggesting a significant accumulation of the nitrogenous waste following the induced ischemia/reperfusion injury. However, there was no significant difference in the creatinine levels.

Renal Histopathology

The animals that died earlier did not show any significant histologic changes, in the 'injured' necrosis. Surprisingly, the BSA 'treated' rat showed even more pathologic changes than the saline control vehicle (data not shown) suggesting that administration of bovine serum albumin (BSA) did not only fail to provide any protection but also contributed further and unanticipated damage.

Procedure-3

Serum Urea Nitrogen

Surprisingly, the serum BUN levels post ischemia/reperfusion injury was unequivocally low group were H & E stained and interpreted by an expert. The liver histology revealed normal cytology and tissue architecture.

It is very likely that the second possibility, starvation, was the reason as the animals were their weight (the average weight loss was 18 grams).

Complement Analysis

The serum complement level before and following ischemia reperfusion injury was analysed stimulate hyperactivation of the classical component of complement pathway and the administered rVCP did not inhibit the classical pathway of complement activation suggesting that the subcutaneous (SC) route is not an effective route for systemic delivery. This was in agreement to previously obtained outcomes (Pers. Comm. Scott A. Smith, University of Louisville, Ky.). However, because renal ischemia/reperfusion injury predominantly involves the alternative but not the classical complement pathway, this observation may only have peripheral importance.

Renal Histopathology

The 45 minutes bilateral clamping approach did not induce a fine ischemia/reperfusion injury Procedure-4

Serum Creatinine and BUN

As shown in FIG. 7 below, there was considerable differences (1.2-fold±0.127) in the serum creatinine levels between the untreated injured (PBS) group and the VCP treatment group, suggesting that the VCP improved renal function and enabled the renal system to excrete the metabolic waste better than the equally injured animals in the untreated group. The sham group displayed the lowest serum creatinine levels as expected. However, there was no statistically significant difference in the serum urea and creatinine levels among any of the groups.

Interestingly, the bilaterally clamped animal showed a 2.9-fold rise in serum creatinine and a 25.3-fold rise in serum BUN levels after 24 hours of I/R injury compared to its baseline concentrations suggesting that acute renal failure (ARF) was induced in this animal.

Renal Histopathology

FIGS. 8, 9 and 10 show the representative renal histologies of the sham, VCP and PBS groups respectively. In the sham group, the tissue displayed normal glomerular (not shown in Figure) and tubular histology (FIGS. 8A & B) in both kidneys. In the VCP group (FIG. 9B), focal necrosis of the tubular epithelial cells was observed in ⅚ (83%) of the animals compared to the markedly elevated and diffuse necrosis of the tubular epithelium in the PBS group (FIG. 10B). The uninjured kidneys were stained for intra-group comparison (FIG. 9A for the VCP & FIG. 10A for the PBS group). The representative right kidneys from each group were displayed for inter-group comparison (FIG. 11A-C).

The C3 immunostaining for the VCP group showed minimal and extremely focal (<5%) C3 deposition in the epithelium of the injured kidney (FIG. 13A). However, the PBS group displayed a strong tubular epithelium stain (25-50%) in the injured kidney (FIG. 13B) suggesting high levels of C3 deposition in the renal tubules following I/R injury. The sham group (FIG. 13C) and the left (uninjured) kidneys of the VCP and the PBS group showed only basal staining between the epithelia.

Procedure-5

Blood Urea Nitrogen (BUN)

As shown in FIG. 14 below, there were substantial differences (3.7-fold) in the serum BUN levels between the authentic VCP treatment group and the untreated injured (PBS) group suggesting the effective therapeutic potential of VCP. Moreover, there was about 1.73-fold lower accumulation of urea in the yeast cell derived humanized recombinant VCP (hrVCP) treated animals compared to the PBS group suggesting further the therapeutic value of the modified recombinant protein.

The Tabular Summary of the creatinine and BUN concentrations and their significance is shown in Table 2 below Serum Creatinine Concentration The creatinine study also showed significant rise in the PBS group suggesting the failure of the kidneys to excrete the metabolic waste. However, following treatment with the authentic VCP or the humanized recombinant VCP (hrVCP), the levels of serum creatinine dropped by about 8.5-fold and 11.6-fold respectively (FIG. 15) suggesting the therapeutic role of the complement inhibitors.

TABLE 2

Geometric Mean of serum Creatinine and BUN concentrations following 24 hours renal ischemia/reperfusion (I/R) injury in rats

| Group | Creatinine (μmol/lt) | BUN (mg/dlt) | Remark |
| --- | --- | --- | --- |
| VCP | 4 | 35.3 | elevated |
| hrVCP | 7 | 70.59 | elevated |
| PBS | 60 | 127.65 | highly elevated |
| Sham | 2 | 2.06 | normal |

Renal Histopathology

The interpretation of the renal histologies by a blinded pathologist revealed that all the PBS group experienced severe and diffuse tubular necrosis (3+ to 4+) in the cortex involving the medulla following the ischemia/reperfusion injury. The severity of injury was equivalent in both kidneys suggesting that acute renal failure was induced. However, following treatment with VCP or hrVCP, the necrosis was correspondingly focal (1+ to 2+) and limited to the cortex (FIG. 16) indicating the beneficial role of intervention with VCP/hrVCP. The sham group A showed normal renal architecture (0 injury score) in both kidneys.

Early Migration of Inflammatory Cells

Interestingly, the PBS group showed aggregation of few neutrophils suggesting early migration of inflammatory cells (FIG. 17). However, there was no any neutrophil in the Sham or the VCP/hrVCP groups indicating that VCP/hrVCP inhibited aggregation of inflammatory cells to the site of injury following 24 hours ischemia/reperfusion injury.

Immunohistochemistry

In accordance with the previous findings (FIG. 13) and the literature described above, there was a direct relationship between C3 deposition and tubular injury. The PBS group showed extensive C3 deposition in the renal tubules following 24 hours I/R injury. However, the VCP/hrVCP treatment has abrogated the local C3 deposition (FIG. 18). The sham group displayed only basal levels of C3 between the epithelia.

DISCUSSION

The ever-increasing advance in molecular biology and proteomics has helped researchers to understand and manipulate several human and non-human proteins. A significant identity between human and some orthopoxviral proteins has been noticed for more than a decade. These proteins known as complement control proteins (CCPs) together with their mammalian homologs belong to the family of regulators of complement activation (RCA). However, there are considerable differences in terms of their biological activity and more interestingly, there is host discrimination between some of the well-studied poxviral complement control proteins such as VCP and SPICE. Despite their sharing of more than 95% amino acid identity, the remaining 11 amino acid differences seem to have created a preferential advantage for SPICE in inactivating the human C3b to a nearly 100-fold more potency. However, it has recently been reported that SPICE is nearly 1000-fold more active than VCP in inhibiting the lipopolysaccharide (LPS) induced activation of the alternative complement pathway by measuring bound human C3b in an ELISA-based assay. It was reasonable to assume that not all the 11 amino acid differences between VCP and SPICE are equally crucial in conferring SPICE's potency, as some of them are not surface-exposed/less exposed than the others. It has been previously shown that the reversion of the amino acid tyrosine (Tyr) at position 98 in MCP has attenuated its C4b cofactor activity.

Recently, the substitution of Tyr in VCP at this position has been shown to increase the complement regulatory activity by 28-fold making it a good target for mutagenesis studies to replace the corresponding amino acid His-98 in VCP towards its MCP and SPICE homologs. It has also been demonstrated that the amino acid residues (94-103) in SPICE and VCP are important in C3b/C4b interaction. Moreover, a recent modeling study has revealed that His-98 and Glu-102 are surface-exposed and therefore expected to create a redundant interface for C3b/C4b interaction.

The amino acid residue Glu-108 in VCP is also visualized as surface-exposed and anticipated to contact C3b/C4b. Moreover, it has been reported that a 17-fold increased potency in modulating the alternative pathway of complement activation by substituting the amino acid at this position to its SPICE analog (Glu-108-Lys) rendering it an important residue for modification. In addition, the amino acid Glu-120 in VCP is also expected to interact with both C3b and C4b and Lys-120 has substituted this residue in both CR1 and SPICE. Moreover, amino acid residue substitution at this position has been shown to affect C4b cofactor activity in MCP. The generation of the mutant protein with the substitution of the single amino acid at this position to its SPICE analog (VCP-E120K) has been shown to immensely enhance the ability of the modified protein to regulate the alternative pathway of complement activation as high as 87-fold. It was therefore based on these evidences and inferences that we generated the single $^{rVCP}$E108K and the triple $^{rVCP}$H98Y,E102K,E120K mutants that possess between 25 and 100-fold more in vitro potency than the recombinant VCP (rVCP) respectively. This enhancement in VCP's activity is achieved most likely because, as suggested recently, the one and the three amino acid substitution(s) increased the overall basic amino acid content of the modified proteins and reduced the acidic (negative) electrostatic potential at the second module (SCR-2). The in vivo role of these modified proteins remain to be elucidated. However, the augmented hemolysis assay based activity suggests their promising potential in modulating complement mediated inflammatory conditions. Especially those that are predominantly driven by the classical pathway of complement activation as in the pig-to-baboon organ xenotransplantation (extensively reviewed elsewhere in the book). The significantly increased ability to regulate the zymosan-induced alternative pathway of complement activation promises a candid potential in attenuating complement mediated ailments predominantly driven by the alternative complement pathway such as the guinea pig-to-rat cardiac xenotransplantation, renal reperfusion injury and zymosan-induced multiple organ dysfunction syndrome (MODS). Moreover, the overall increase in the number of putative heparin binding sites might have biologically privileged the triple $^{rVCP}$H98Y,E102K,E120K mutant. The in vitro ability of VCP to inhibit zymosan-induced complement activation was first demonstrated by Mahesh et al.

LIST OF ABBREVIATIONS

AOX-1: alcohol oxidase-1
AP: Alternative pathway
BMGY: buffered minimal glycerol medium
BMMY: buffered minimal methanol medium
C4-BP: C4-binding protein
CCP: complement control protein
CR-1: complement receptor type-1
CP: Classical Pathway
DAF: decay-accelerating factor
$IC_{50}$: Inhibitory concentration at 50%
IMP: inflammation modulatory protein
LPS: lipopolysaccharide
MCP: membrane cofactor protein
ng: nano gram
ORF: open reading frame
PCR: polymerase chain reaction
RCA: regulator of complement activation
rVCP: recombinant vaccinia virus complement control protein
hrVCP: humanized recombinant vaccinia virus complement control protein
SDS-PAGE: sodium dodecyl sulphate polyacrylamide gel electrophoresis
SPICE: smallpox inhibitor of complement enzymes
ssRBC: sensitised sheep red blood cells

SEQUENCE LISTING

```
<160> NUMBER OF SEQ ID NOS: 6

<210> SEQ ID NO 1
<211> LENGTH: 840
<212> TYPE: DNA
<213> ORGANISM: Vaccinia virus

<400> SEQUENCE: 1
tttttattat ttgtacgatg tccaggataa cattttttacg gataaataaa tatgaaggtg      60
gagagcgtga cgttcctgac attgttggga ataggatgcg ttctatcatg ctgtactatt     120
ccgtcacgac ccattaatat gaaatttaag aatagtgtgg agactgatgc taatgctaat     180
tacaacatag gagacactat agaatatcta tgtctacctg gatacagaaa gcaaaaaatg     240
ggacctatat atgctaaatg tacaggtact ggatggacac tctttaatca atgtattaaa     300
cggagatgcc catcgcctcg agatatcgat aatggccaac ttgatattgg tggagtagac     360
tttggctcta gtataacgta ctcttgtaat agcggatatc atttgatcgg tgaatctaaa     420
tcgtattgtg aattaggatc tactggatct atggtatgga atcccgaggc acctatttgt     480
gaatctgtta aatgccaatc ccctccatct atatccaacg gaagacataa cggatacgag     540
gatttttata ccgatgggag cgttgtaact tatagttgca atagtggata ttcgttgatt     600
ggtaactctg gtgtcctgtg ttcaggagga gaatggtccg atccacccac gtgtcagatt     660
gttaaatgtc cacatcctac aatatcaaac ggatacttgt ctagcgggtt taaaagatca     720
tactcataca acgacaatgt agactttaag tgcaagtacg gatataaact atctggttcc     780
tcatcatcta cttgctctcc aggaaataca tggaagccga aacttccaaa atgtgtacgc     840
```

<210> SEQ ID NO 2
<211> LENGTH: 244
<212> TYPE: PRT
<213> ORGANISM: Vaccinia virus

<400> SEQUENCE: 2

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 3
<211> LENGTH: 244
<212> TYPE: PRT
<213> ORGANISM: Artificial
<220> FEATURE:
<223> OTHER INFORMATION: Recombinant Modified VCP Sequence Originating
      from Vaccinia Virus

<400> SEQUENCE: 3

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

-continued

```
Gly Gly Val Asp Phe Gly Ser Ser Ile Thr Tyr Ser Cys Asn Ser Gly
                 85                  90                  95

Tyr His Leu Ile Gly Glu Ser Lys Ser Tyr Cys Lys Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 4
<211> LENGTH: 244
<212> TYPE: PRT
<213> ORGANISM: Artificial
<220> FEATURE:
<223> OTHER INFORMATION: Recombinant Modified VCP Sequence Originating
      from Vaccinia Virus

<400> SEQUENCE: 4

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Lys Ser Lys Ser Tyr Cys Glu Leu Gly Ser Thr
            100                 105                 110

Gly Ser Met Val Trp Asn Pro Lys Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190
```

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
        210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 5
<211> LENGTH: 244
<212> TYPE: PRT
<213> ORGANISM: Artificial
<220> FEATURE:
<223> OTHER INFORMATION: Recombinant Modified VCP Sequence Originating
      from Vaccinia Virus

<400> SEQUENCE: 5

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Ser Lys Ser Tyr Cys Glu Leu Gly Ser Thr
            100                 105                 110

Gly Ser Met Val Trp Asn Pro Lys Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 6
<211> LENGTH: 244
<212> TYPE: PRT
<213> ORGANISM: Artificial
<220> FEATURE:
<223> OTHER INFORMATION: Recombinant Modified VCP Sequence Originating
      from Vaccinia Virus -continued

```
<400> SEQUENCE: 6

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
            35                  40                  45

Ala Lys Cys Thr Gly Thr Gly Trp Thr Leu Phe Asn Gln Cys Ile Lys
        50              55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Ser Lys Ser Tyr Cys Lys Leu Gly Ser Thr
            100                 105                 110

Gly Ser Met Val Trp Asn Pro Lys Ala Pro Ile Cys Glu Ser Val Lys
            115                 120                 125

Cys Gln Ser Pro Pro Ser Ile Ser Asn Gly Arg His Asn Gly Tyr Glu
        130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
            195                 200                 205

Asp Asn Val Asp Phe Lys Cys Lys Tyr Gly Tyr Lys Leu Ser Gly Ser
        210                 215                 220

Ser Ser Ser Thr Cys Ser Pro Gly Asn Thr Trp Lys Pro Glu Leu Pro
225                 230                 235                 240

Lys Cys Val Arg
```

The invention claimed is:

1. An isolated recombinant vaccinia virus complement control protein (hrVCP) polypeptide comprising a modified amino acid sequence comprising one or more amino acid substitutions to an amino acid sequence as set forth in SEQ ID NO: 2, wherein the one or more amino acid substitutions are selected from the group consisting of H98Y, E102K, E108K, E120K, and combinations thereof, provided at least one of the substitutions is E102K, and wherein the hrVCP polypeptide exhibits a complement activation regulatory activity greater than a complement activation regulatory activity of a polypeptide comprising the amino acid sequence as set forth in SEQ ID NO: 2.

2. The hrVCP polypeptide of claim 1, wherein the modified amino acid sequence comprises at least two amino acid substitutions.

3. The hrVCP polypeptide of claim 1, wherein the modified amino acid sequence comprises at least three amino acid substitutions.

4. The hrVCP polypeptide of claim 1, wherein the modified amino acid sequence comprises an amino acid sequence of SEQ ID NO: 4.

5. The hrVCP polypeptide of claim 1, wherein the complement activation regulatory activity comprises regulating activation of a classical complement activation pathway, an alternative complement activation pathway, or both the classical and alternative complement activation pathways.

6. The hrVCP polypeptide of claim 5, wherein regulating activation of the classical complement activation pathway, the alternative complement activation pathway, or both the classical and alternative complement activation pathways comprises inhibiting activation of at least one complement component, inhibiting activity of at least one activated complement component, or combinations thereof.

7. The hrVCP polypeptide of claim 6, wherein the complement component comprises C3 or C4 and the activated complement component comprises C3b or C4b.

8. An isolated nucleic acid encoding an hrVCP polypeptide of claim 1.

9. A method of producing a recombinant vaccinia virus complement control protein (hrVCP) polypeptide having enhanced complement activation regulatory activity, comprising:

a. providing a nucleotide sequence encoding vaccinia virus complement control protein (VCP) polypeptide comprising an amino acid sequence as set forth in SEQ ID NO: 2; and b. substituting one or more amino acids of the VCP polypeptide amino acid sequence to produce a nucleotide sequence encoding a recombinant vaccinia virus complement control protein (hrVCP) polypeptide having enhanced complement activation regulatory activity when compared to a complement activation regulatory activity of the VCP polypeptide, wherein the one or more amino acids substituted are selected from the group consisting of H98Y, E102K, E108K, E120K, and combinations thereof, provided at least one of the amino acids substituted is E 102K, and c. expressing the nucleotide sequence of (b) to produce the recombinant protein.

10. The method of claim 9, wherein the hrVCP polypeptide comprises at least two amino acid substitutions.

11. The method of claim 9, wherein the hrVCP polypeptide comprises at least three amino acid substitutions.

12. The method of claim 9, wherein the hrVCP polypeptide comprises an amino acid sequence of SEQ ID NO: 4.

13. The method of claim 9, wherein the complement activation regulatory activity comprises regulating activation of a classical complement activation pathway, an alternative complement activation pathway, or both the classical and alternative complement activation pathways.

14. The method of claim 13, wherein regulating activation of the classical complement activation pathway, the alternative complement activation pathway, or both the classical and alternative complement activation pathways comprises inhibiting activation of at least one complement component, inhibiting activity of at least one activated complement component, or combinations thereof.

15. The method of claim 14, wherein the complement component comprises C3 or C4 and the activated complement component comprises C3b or C4b.

16. A method of treating a disorder in a subject resulting from complement-mediated inflammation, comprising administering to the subject a therapeutically effective amount of an hrVCP polypeptide of claim 1, or a pharmaceutically acceptable salt thereof.

17. The method of claim 16, wherein the subject is a human.

18. The method of claim 16, wherein administering to the subject the hrVCP polypeptide comprises intravenously injecting into the subject the hrVCP polypeptide.

19. The method of claim 16, wherein the therapeutically effective amount of the hrVCP polypeptide ranges from about 0.01 g/kg to about 0.1 g/kg per dose.

20. A method of reducing or inhibiting activation of complement in a subject, comprising administering to the subject an effective amount of an hrVCP polypeptide of claim 1.

21. The method of claim 20, wherein reducing or inhibiting activation of complement comprises reducing or inhibiting activation of a classical complement activation pathway, an alternative complement activation pathway, or both the classical and alternative complement activation pathways.

22. The method of claim 21, wherein reducing or inhibiting activation of the classical complement activation pathway, the alternative complement activation pathway, or both the classical and alternative complement activation pathways comprises inhibiting activation of at least one complement component, inhibiting activity of at least one activated complement component, or combinations thereof.

23. The method of claim 22, wherein the complement component comprises C3 or C4 and the activated complement component comprises C3b or C4b.

24. The method of claim 20, wherein the subject is a human.

25. The method of claim 20, wherein administering to the subject the hrVCP polypeptide comprises intravenously injecting into the subject the hrVCP polypeptide.

26. The method of claim 20, wherein the therapeutically effective amount of the hrVCP polypeptide ranges from about 0.01 g/kg to about 0.1 g/kg per dose.

27. A pharmaceutical composition comprising an hrVCP polypeptide of claim 1 and a pharmaceutically acceptable carrier or excipient.

* * * * *